US006639201B2

(12) United States Patent
Almogy et al.

(10) Patent No.: US 6,639,201 B2
(45) Date of Patent: Oct. 28, 2003

(54) SPOT GRID ARRAY IMAGING SYSTEM

(75) Inventors: Gilad Almogy, Givataim (IL); Oren Reches, Zoran (IL)

(73) Assignee: Applied Materials, Inc., Santa Clara, CA (US)

( * ) Notice: Subject to any disclaimer, the term of this patent is extended or adjusted under 35 U.S.C. 154(b) by 114 days.

(21) Appl. No.: 09/986,138

(22) Filed: Nov. 7, 2001

(65) Prior Publication Data

US 2003/0085335 A1 May 8, 2003

(51) Int. Cl.$^7$ ............................................... H01L 27/00
(52) U.S. Cl. ............................. 250/208.1; 250/559.45
(58) Field of Search .................... 250/208.1, 559.45, 250/559.4, 559.3, 548, 201.3; 355/53–55; 356/399–401

(56) References Cited

U.S. PATENT DOCUMENTS

| 5,200,766 | A | * | 4/1993 | Iwasaki ....................... 347/261 |
| 5,248,876 | A |   | 9/1993 | Kerstens et al. |
| 5,900,637 | A |   | 5/1999 | Smith |
| 6,248,988 | B1 |  | 6/2001 | Krantz |

FOREIGN PATENT DOCUMENTS

EP          0 871 052          3/1998

OTHER PUBLICATIONS

M. Feldman, "Projection X–Ray Lithography Using Arrays of Zone Plates," British Library, May 21, 2001, pp. 136–144.

Ihsan J. Djomehri, T.A. Savas, and Henry I. Smith, "Zone–Plate–Array Lithography In The Deep Ultraviolet," J. Vac. Sci. Technol. B, 16(6), Nov./Dec. 1998, pp. 3426–3429.
D.J.D. Carter, Dario Gil, R. Menon, Ihsan J. Djomehri, and Henry I. Smith, "Zone–Plate Array Lithography (ZPAL): A New Maskless Approach," Part of the SPIE Conference on Emerging Lithographic Technologies III, Mar. 1999, pp. 324–332.

(List continued on next page.)

Primary Examiner—Que T. Le
(74) Attorney, Agent, or Firm—McDermott, Will & Emery

(57) ABSTRACT

A high data-rate spot-grid array imaging system is provided that compensates for stage vibrations and overcomes the severe linearity requirements of prior art systems. Embodiments include an imaging system with a two-dimensional and periodic array of lenses, each lens imaging a spot in an object plane, such as a semiconductor substrate to be inspected, upon an image plane to image a two-dimensional and periodic array of spots. A sensor is provided in a conjugate image plane with a two-dimensional and periodic array of readout elements, each collecting the signal from one of the spots. A mechanical system moves the substrate in a direction which is nearly parallel to an axis of the array of spots such that as the substrate is moved across the spot array in the scan direction (the y-direction) the spots trace a path which leaves no gaps in the mechanical cross-scan direction (the x-direction). A compensator, such as a servo or a movable mirror, compensates for mechanical inaccuracies in the moving stage, thereby increasing imaging accuracy. In other embodiments, the motion of the mechanical system provides a small overlap between coverage areas of lenses of the lens array in consecutive columns, thereby overcoming the severe linearity requirements of prior art systems and allowing the utilization of cost effective microlens arrays.

80 Claims, 14 Drawing Sheets

OTHER PUBLICATIONS

M. Feldman, "Use of Zone Plate Arrays in Projection X-Ray Lithography," OSA Proceeding On X-Ray Projection Lithography, May 21, 2001, vol. 18, pp. 207–209.

Henry I. Smith, "A Proposal For Maskless, Zone-Plate-Array Nanolithography," J. Vac. Sci. Technol. B 14(6), Nov./Dec. 1996, pp. 4318–4322.

D.J.D. Carter, Dario Gil, Rajesh Menon, Mark K. Mondol, and Henry I. Smith, "Maskless, Parallel Patterning With Zone-Plate Array Lithography," J. Vac. Sci. Technol. B 17(6), Nov./Dec. 1999, pp. 3449–3452.

Hans J. Tiziani, Michael Wegner, Daniela Steudle, "Confocal Principle For Macro- And Microscopic Surface And Defect Analysis," Opt. Eng. 39(1), Jan. 2000, pp. 32–39.

Dario Gil, Rajesh Menon, D.J.D. Carter, and Henry I. Smith, "Lithographic Patterning And Confocal Imaging With Zone Plates," J. Vac. Sci. Technol. B. 18(6), Nov./Dec. 2000, pp. 2881–2885.

D.J.D. Carter, Dario Gil, Rajesh Menon, Mark K. Mondol, And Henry I. Smith, "Maskless, Parallel Patterning With Zone-Plate Array Lithography," J. Vac, Sci. Technol. B 17(6), Nov./Dec. 1999, pp. 3449–3452.

H.J. Tiziani, R. Achi, R.N. Kramer, and L. Wiegers, "Theoretical Analysis Of Confocal Microscopy With Microlenses," Applied Optics, vol. 35, No. 1, Jan. 1, 1996, pp. 120–125.

* cited by examiner

SPOT GRID ARRAY IMAGING SYSTEM

RELATED APPLICATIONS

The present application is related to Applicants' co-pending application Ser. No. 09/986,137, entitled SPOT GRID ARRAY ELECTRON IMAGING SYSTEM, filed Nov. 7, 2001

FIELD OF THE INVENTION

The present invention relates to an imaging system. The present invention has particular applicability in optical imaging systems optimized for automated defect inspection.

BACKGROUND ART

Optical imaging involves the reproduction or imaging of a scaled image in an object plane upon an image plane. High-resolution imaging is termed microscopy. Such imaging is refered to as "electronic imaging" when an optoelectronic device such as an array of charged coupled devices (called a "CCD") is used to sample the optical signal in the image plane and translate it into an electrical signal.

Automated optical inspection is a technique for measuring the integrity of an object by collecting an image of it and comparing that image to a reference (e.g., comparing a die to a data-base for photolithographic masks), to another part of that object (such as die-to-die inspection for semiconductor wafers), or to a reference image (die-to-"golden image"). Disadvantageously, when conducting high-resolution inspection of large semiconductor substrates, the FOV of the imaging system cannot cover the entire substrate to be inspected, so the substrate must be moved or "stepped" across the FOV, thereby increasing inspection time. To increase throughput, some conventional automated inspection tools continuously scan the substrate in one direction while imaging an orthogonal one-dimensional optical FOV. Once the substrate is traversed in the scanning direction, it is typically moved in the other (cross-scan) direction by a distance of one FOV, and then its path is retraced, creating a serpentine motion path.

Other optical imaging systems for inspecting semiconductor substrates utilize a "spot grid array" to achieve high throughput. In these systems, an imager typically includes a two-dimensional and periodic array of lenses, each lens imaging a spot in an object plane, such as a substrate to be inspected, upon an image plane to image a two-dimensional and periodic array of spots from the object plane upon the image plane. A sensor, such as a CCD, is provided in a conjugate image plane with a two-dimensional and periodic array of readout elements, each collecting the signal from a spot in the object plane. A mechanical system moves the substrate such that as the substrate is moved across the spot array in the scan direction (the y-direction) the spots trace a path which leaves no gaps in the mechanical cross-scan direction (the x-direction). Thus, imaging of very large FOVs is accomplished by employing an array of optical elements each having a minimal FOV, rather than complex large-FOV optics. Optical imaging devices utilizing a spot grid array are described in U.S. Pat. No. 6,248,988 to Krantz, U.S. Pat. No. 6,133,986 to Johnson, U.S. Pat. No. 5,659,420 to Wakai, and U.S. Pat. No. 6,043,932 to Kusnose.

These and other previous implementations of spot-grid array concepts suffer from several limitations. To achieve the very high data-rates required for high-end inspection with all-mechanical stage scanning, a large array is required. For example, a data-rate of 10 Gpix/sec with a 100 nm pixel and a 32×32 lens array requires a stage velocity of 100 nm×($10×10^9$)/(32×32) m/sec, which is impractical due to the stage-turn around time, the motion accuracy requirement and the stage complexity and cost. To reduce the required speed to a more reasonable stage speed, a larger array is needed. A 320×320 array, for example, requires a stage speed of 10 mm/sec, which is a very reasonable rate. Moreover, the frame-rate would be reduced to 100 KHz, vs. 10 MHz for a 32×32 array. The lower data rate is compatible with the pulse rate of Q-switched lasers (i.e., several tens of KHz), which thus enables using high-efficiency frequency conversion for short wavelength and hence high-resolution imaging. By using a somewhat larger array (for example 1000×1000), the frame-rate (pulse-rate) requirement is further reduced (to 10 KHz), enabling the use of Excimer lasers (such as a 157 nm F2 laser) and thus even finer resolution.

However, some major problems prevent the use of prior art technologies for large arrays, such as stage vibrations, relatively limited focus capabilities, imaging linearity, dielectric layer interference, and limited fault detection and classification capabilities. Each of these problems will now be discussed in turn.

The magnitude of stage mechanical vibrations increases with the time passed between adjacent pixels. This time is equal to the reciprocal of the frame-rate multiplied by the number of rows in the array. For the 10 GPS and 320×320 array scenario discussed above, this is 3 millisecond, vs. 3 microseconds for a 32×32 array. Image processing cannot be used to compensate for these vibrations, because parts of the image can be missing, thereby reducing accuracy. It is noted that electron imaging systems are more susceptible to stage mechanical vibrations as the mechanical stage move in vacuum.

A further limitation of prior art spot grid array implementations arises from the fact that inspecting with confocal imaging requires very tight focus control, which is very difficult to achieve at high scan rates with large NA short-wavelength optics. To overcome this problem, simultaneous multi-height confocal imaging is necessary. However, while taking several height-slice images sequentially, as described in the prior art, is compatible with a one frame review mode, it is not compatible with the continuous motion requirements of inspection systems.

Another limitation to large arrays in the prior art is the linearity requirement on the lens array, imaging optics and detector arrays. To obtain good results from a spot grid array system, close tolerances on the linearity of the optics is important—both for the microlens array and for the de-magnification optical elements. The optical spots must be located on an exactly rectilinear grid with very exact distances between the spots. Such extreme linearity is difficult and expensive to achieve.

Another limitation of prior art technology is the need to employ a coherent laser source to achieve sufficient power density for high-speed inspection. Many inspected substrates are covered by transparent or semi-transparent dielectric layers, which cause interference phenomena between the surfaces of the dielectric layers. As the thickness of these layers varies across the wafer, the phase of the reflections of the coherent light from the top and bottom of the dielectric layer varies. Moreover, the interference can be either constructive or destructive. These interference phenomena cause a change in the reflected power despite the absence of defects or irregularities, limiting the accuracy of defect detection and thereby limiting the capability of the system to identify true defects.

A further limitation of prior art spot grid array techniques arises from the limited fault detection and classification ability resulting from the collection of light signals from a single angular section of an object. As a result, fault detection and analysis may require more than a single inspection, thus dramatically increasing the amount of data that needs to be processed and collected for reliable detection and classification of faults.

There exists a need for a low-cost, accurate, high-speed imaging system with a large FOV for reducing manufacturing costs and increasing production throughput.

SUMMARY OF THE INVENTION

The present invention provides a high data rate spot grid array imaging system that compensates for stage vibrations.

The present invention further provides a high data rate spot grid array imaging system having a small overlap between coverage areas of lenses of a lens array in consecutive columns, thereby overcoming the severe linearity requirements of prior art systems and allowing the utilization of cost effective microlens arrays.

The present invention further provides for the employment of broadband illumination and broad illumination spots to overcome dielectric layers interference without reducing the throughput of the imaging system.

The present invention further provides for the collection of reflected light from the spots formed on the substrate from several directions simultaneously, thereby improving the fault classification and detection capabilities of the imaging system.

The present invention further provides for the simultaneous collection of data from more than one distance from the inspected substrate, thus allowing the selection of one or more relevant data sets out of a plurality of data sets, instead of mechanically moving the substrate upwards or downwards.

Other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other features are achieved in part by an imaging system with a two-dimensional and periodic array of lenses, each lens imaging a spot in an object plane, such as a substrate to be inspected, upon an image plane to image a two-dimensional and periodic array of spots from the object plane upon the image plane. A sensor is provided in a conjugate image plane with a two-dimensional and periodic array of readout elements, each collecting the signal from a spot in the object plane. A mechanical system moves the substrate in a direction nearly parallel to an axis of the array of spots such that as the substrate is moved across the spot array in the scan direction, the spots trace a path which leaves no gaps in the mechanical cross-scan direction. A compensator is provided for compensating for mechanical inaccuracies in the moving stage.

Additional features of the present invention will become readily apparent to those skilled in the art from the following detailed description, wherein only the preferred embodiments of the present invention are shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Figure 1A:
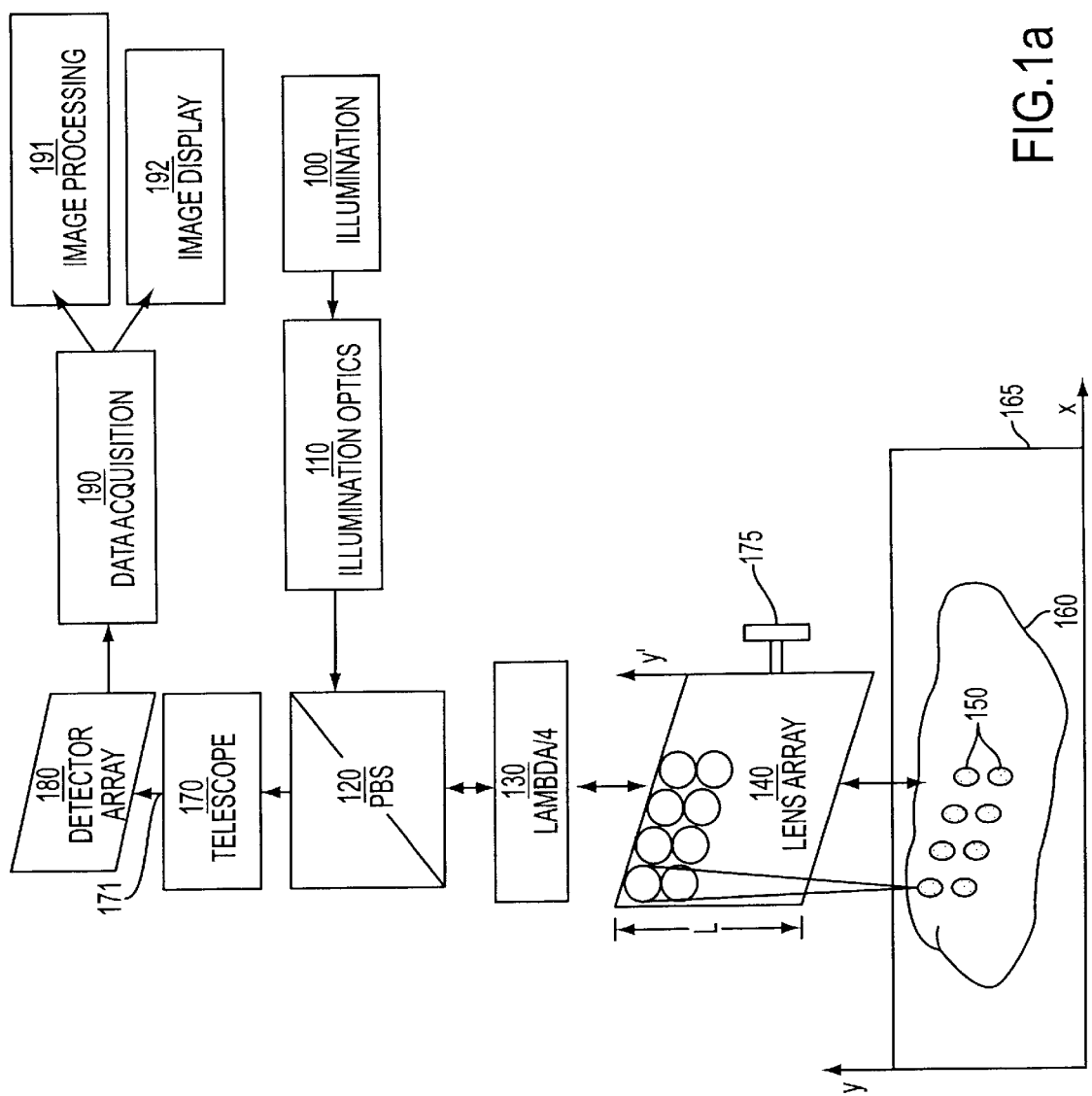
FIGS. 1a–1l schematically illustrate imaging systems in accordance with embodiments of the present invention.

An embodiment of the present invention will now be described with reference to FIGS. 1a and 2. As shown in FIG. 1a, a radiation source such as a light source 100; e.g. at least one laser, diode or lamp, provides a light beam. Illumination optics 110, such as a conventional collimator, collimates the beam and brings it to the desired width. Collimating optics 110 may include a polarizing element to ensure that the light reaches polarizing beam-splitter 120 with the polarization that will reflect the beam into the imaging path. A quarter-wave plate 130 is used to rotate the polarization of the illumination light by 90 degrees. The collimated light impinges upon a lens array 140 where it is focused by the individual elements into an array of separate spots 150 upon an object to be imaged 160, such as a semiconductor substrate. Each element in lens array 140 can be an individual lens, such as a micro-lens, or a multiple lens element. Reflected light from substrate 160 is redirected through lens array 140 and quarter wave-plate 130, and reaches polarizing beam-splitter 120 with a polarization rotated by 90 degrees or half a wavelength with respect to the illumination beam. It therefore passes through polarizing beam-splitter 120. An optical telescope 170 is used to image the back pupil plane of the lens array 140 (which can be the same plane as lens array 140) upon a two-dimensional detector array 180, such as a CCD array corresponding to lens array 140, such that each CCD pixel sees one spot on substrate 160. Signals from detector array 180 are read out by a data acquisition section 190, which can be used to transfer them to an image processing unit 191 and/or an image display unit 192. Telescope 170 can be placed in an intermediate image plane where light reflected from spot array 150 forms an intermediate image substantially equal in size to lens array 140, to demagnify the intermediate image before it reaches detector array 180.

Substrate 160 is carried on a mechanical stage 165 which is moved in the y direction in a direction which is nearly parallel to one of the axes y' of the array of spots 150. The deviation from parallelicity is such that as substrate 160 is moved a distance substantially equal to the length L of the spot array in the scan direction y, the spots trace a path which leaves no gaps in the mechanical cross-scan direction (the x direction).

Several types of lenses can be used in lens array 140, such as standard lenses or microlenses of either the refractive or diffractive type. For relatively low NA's and large FOVs, plastic diffractive elements can be used. This allows for FOVs of many tens of centimeters across or even more. For high NA applications microlens arrays (typically tens of microns across) can be used. If diffractive lens elements are used, the lens array can further contain an aperture array (i.e., a pinhole array) to truncate the higher scattering orders created by the diffractive elements. Diffractive lenses are particularly suitable when used in conduction with short wavelengths of light, such as extreme ultraviolet (EUV) of about 13 nm, to practice the invention.

Moreover, the micro-lens arrays referred to herein, such as lens array 140, can be a single array of lenses, or multiple arrays arranged in series, as per conventional optical techniques, so the optical paths of the individual lens elements from the separate arrays form a compound lens. Such an arrangement results in arrays of compound lenses having a higher numerical aperture than can be obtained with arrays of single lenses. Such compound micro-lens arrays can be mechanically assembled by stacking individual lens arrays, or manufactured by, for example, well-known MEMS (micro-electro mechanical systems) manufacturing techniques.

Figure 2:
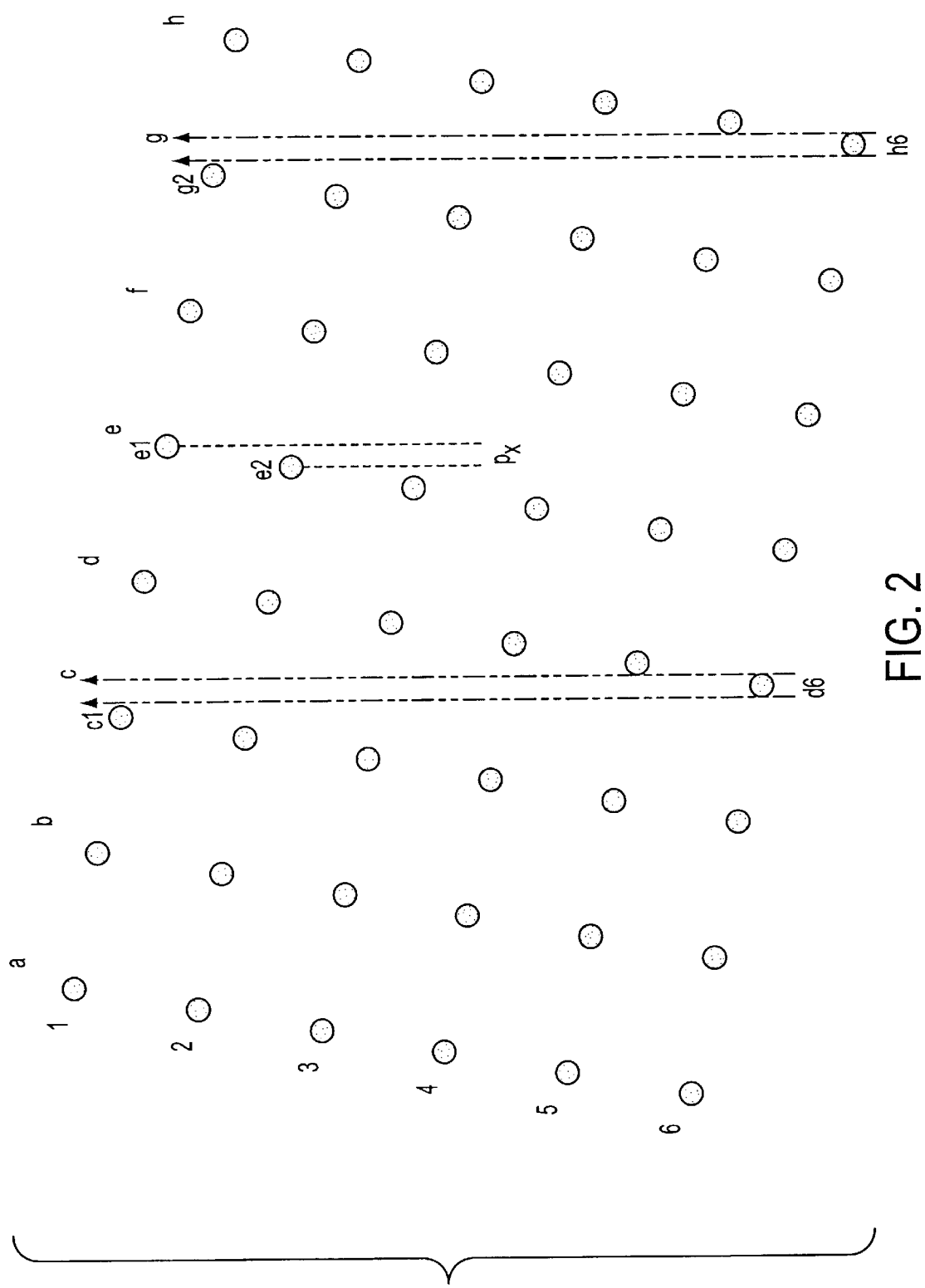
FIG. 2 depicts a spot array on the surface of the object plane produced by the systems of FIGS. 1a–1l.

FIG. 2 schematically depicts spot array 150 in the substrate (object) plane. For simplicity, FIG. 2 shows an 8 wide (a–h) by 6 deep (1–6) array of spots. When practicing the present invention, the array typically comprises at least several hundred lens elements, resulting in a corresponding number of spots. The shift in the mechanical cross-scan x direction between the lens centers of lenses in consecutive lines determines the pixel size in the x direction (i.e., the projection $p_x$ on the x-axis of the distance between the e'th lens in the first line e1 and the e'th lens in the 2nd line e2). The pixel size reflects how densely substrate 160 is sampled. To obtain continuous coverage of substrate 160, the last lens in column d6 must trace a path no more than one pixel away in the cross-scan x direction from the tangent of the first lens in an adjacent column (c1). The pixel size in the mechanical scan y direction $p_y$ (not shown) is determined by the distance traversed between the spot center of a given spot between two consecutive samplings of the detector; that is, the distance between the center of a spot f4 at time 0 ("f4t0") and the same spot one sampling interval later ("f4t1"). This distance is determined by multiplying the stage velocity and sampling interval.

Substrate motion can be achieved by any means ensuring accurate and linear motion, such as can be obtained from a conventional interferometer-controlled stage with linear motors and air-bearings, commercially available from Anorad Corporation of New York. To correct the residual inaccuracy such as that created by mechanical vibrations of the stage, a servo 175 can be included to control an optical element for moving the spot array and compensating for the substrate mis-location. In the embodiment of FIG. 1a, the movable optical element may be the lens array 140 itself. In another embodiment of the present invention, the angle of incidence upon the back pupil of lens array 140 may be changed by means of a movable mirror, an electro-optic or an acousto-optic element in the optical illumination path and/or the collection path.

To ensure the spots 150 are focused on substrate 160, any focus error which needs to be corrected is measured using conventional techniques, as disclosed, for example, in U.S. Pat. No. 6,124,924, the entire disclosure of which is incorporated herein by reference. Correction is then implemented either by moving substrate 160 in the z direction (i.e., up or down in relation to lens array 140), by moving lens array 140, or by another optical element (not shown) which is moved to compensate. If substrate 160 is not planar, lens array 140 or another optical element can be tilted to compensate for the substrate's local (i.e., within FOV) slope.

In the embodiment of the present invention shown in FIG. 1a, either a collimated, partially collimated, or non-collimated illumination source 100 can be used. In an embodiment of the present invention where illumination source 100 is collimated, lens array 140 is placed one focal distance away from substrate 160 to create an array of focused spots 150. If the lens elements of lens array 140 have negligible on-axis aberrations, an array of diffraction-limited spots 150 is obtained. In that case, the role of the collection optics (ref. nos. 120, 130, 140, 170) is to image lens array 140's back pupil on detector array 180 with a resolution requirement determined by the size of the individual lenses in array 140. Since the size of the lenses is typically in the tens of microns to several millimeters range if microlenses are used to make up lens array 140, and the size of the spots 150 is in the tenths of a micron to tens of microns range, the requirement for imaging the back pupil of lens array 140 is much simpler than a requirement to image the entire FOV. Since resolution in this case is obtained by the illumination, illumination source 100 needs to be a laser light source to provide sufficient brightness. This embodiment of the present invention is essentially a laser-scanning microscope where the only scanning element is mechanical stage 165. If a pin-hole 171 is inserted in the focal point of the telescope 170 and aligned with illumination source 100, telescope 170 becomes a confocal microscope.

In embodiments of the present invention where a partially-collimated or non-collimated illumination source 100 is employed, the spots in array 150 are not diffraction limited. In this case, placing pin-hole 171 at the focal point of telescope 170 ensures imaging of diffraction limited spots. This embodiment of the present invention is essentially an array of imaging microscopes each imaging one spot, with the motion of stage 165 used to create continuous coverage of substrate 160.

In another embodiment of the present invention, a standard beam splitter is used in place of polarizing beam splitter 120. Consequently, there is no need for quarter wave plate 130.

Figure 1B:
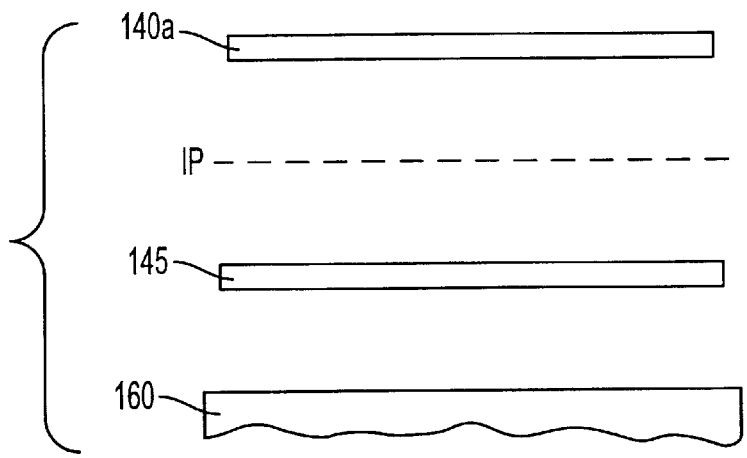
Figure 1C:
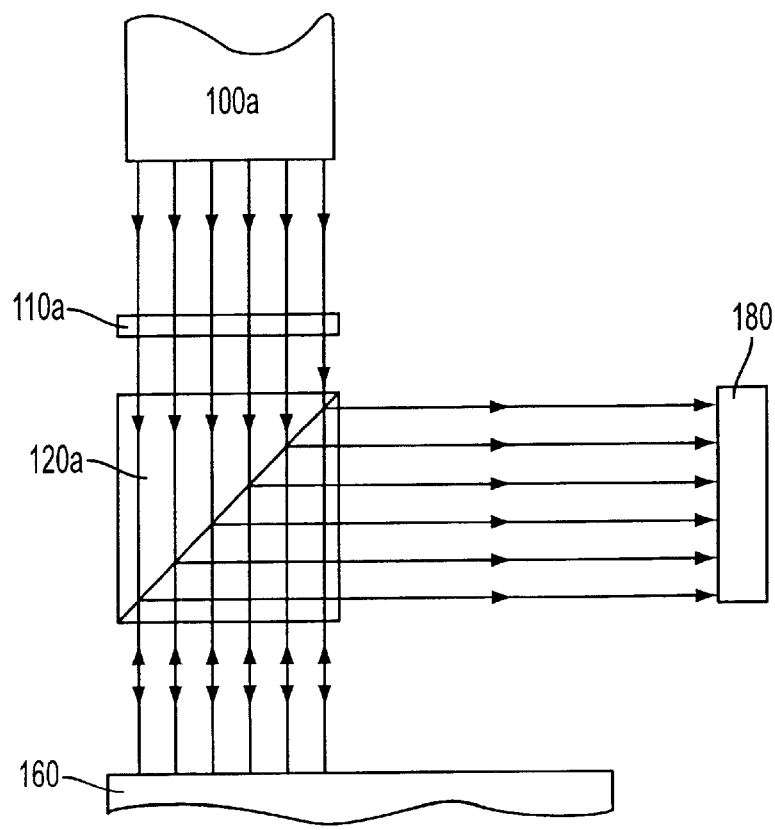
Figure 1D:
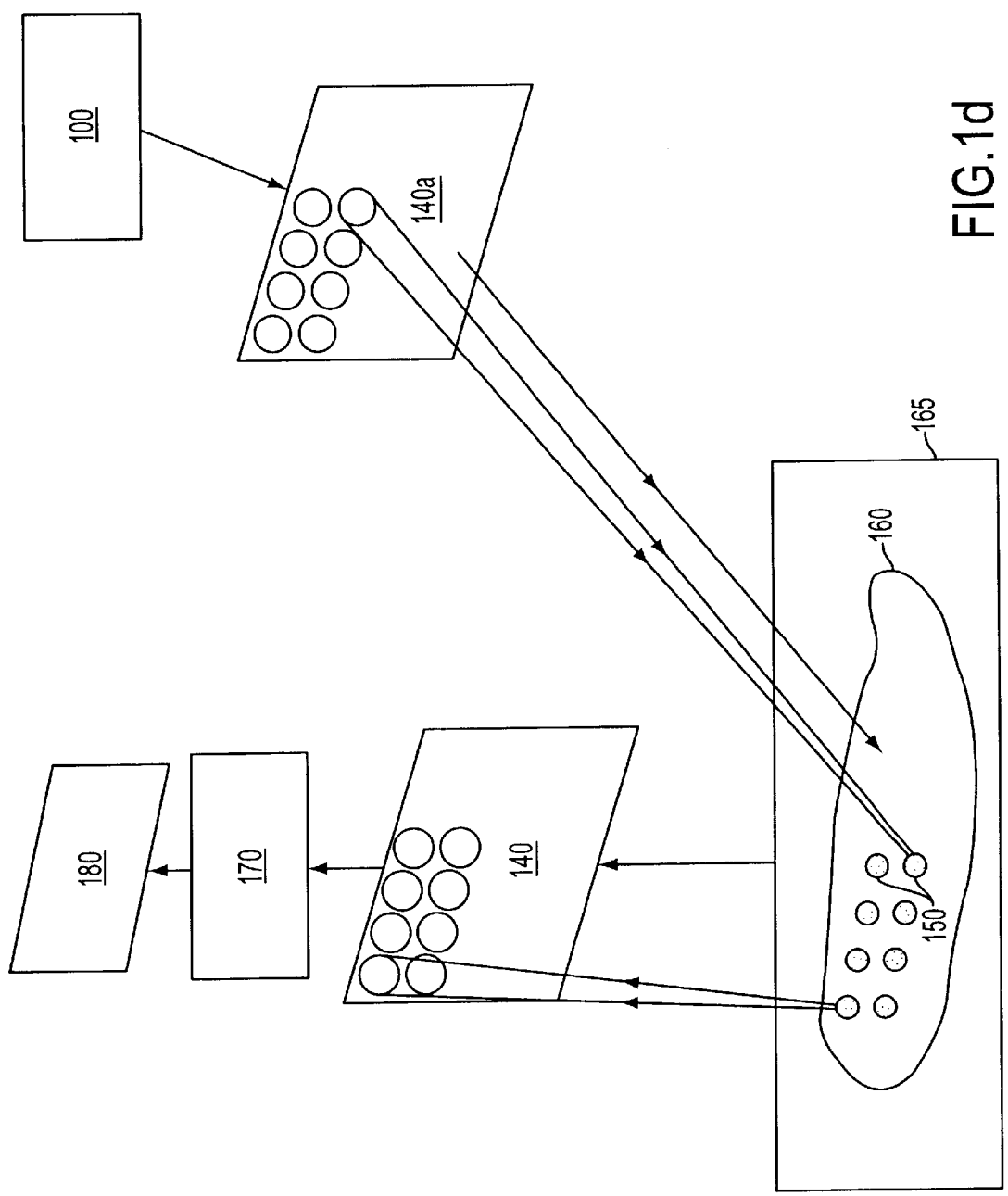

In a further embodiment of the present invention illustrated in FIG. 1d, the illumination path does not pass through lens array 140 but reaches substrate 160 via a different path. That path may be either illumination of all the area of the FOV or include a lens array 140a or an equivalent diffractive optical element as shown to illuminate only the array of spots 150.

Figure 1E:
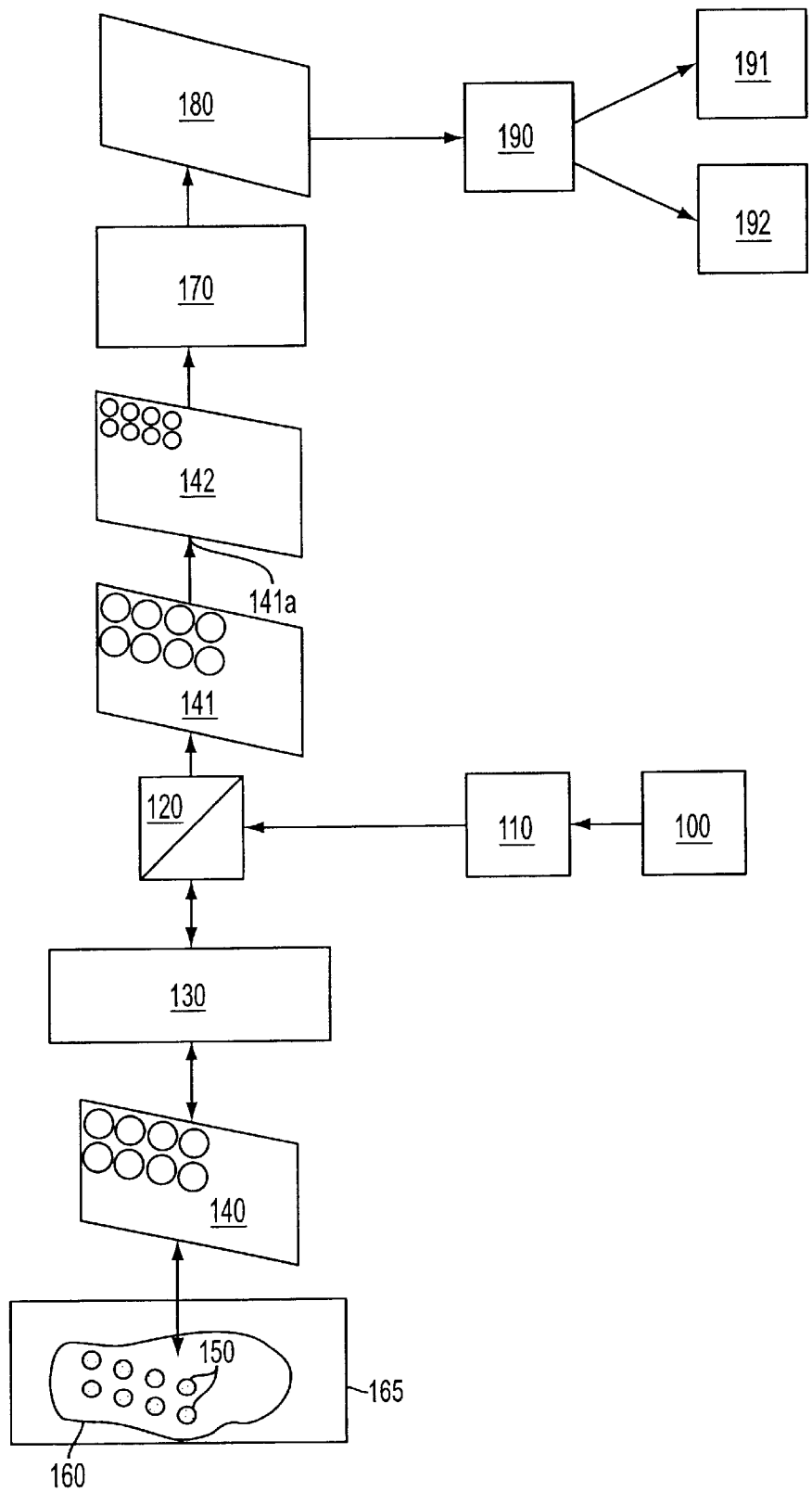
Figure 1F:
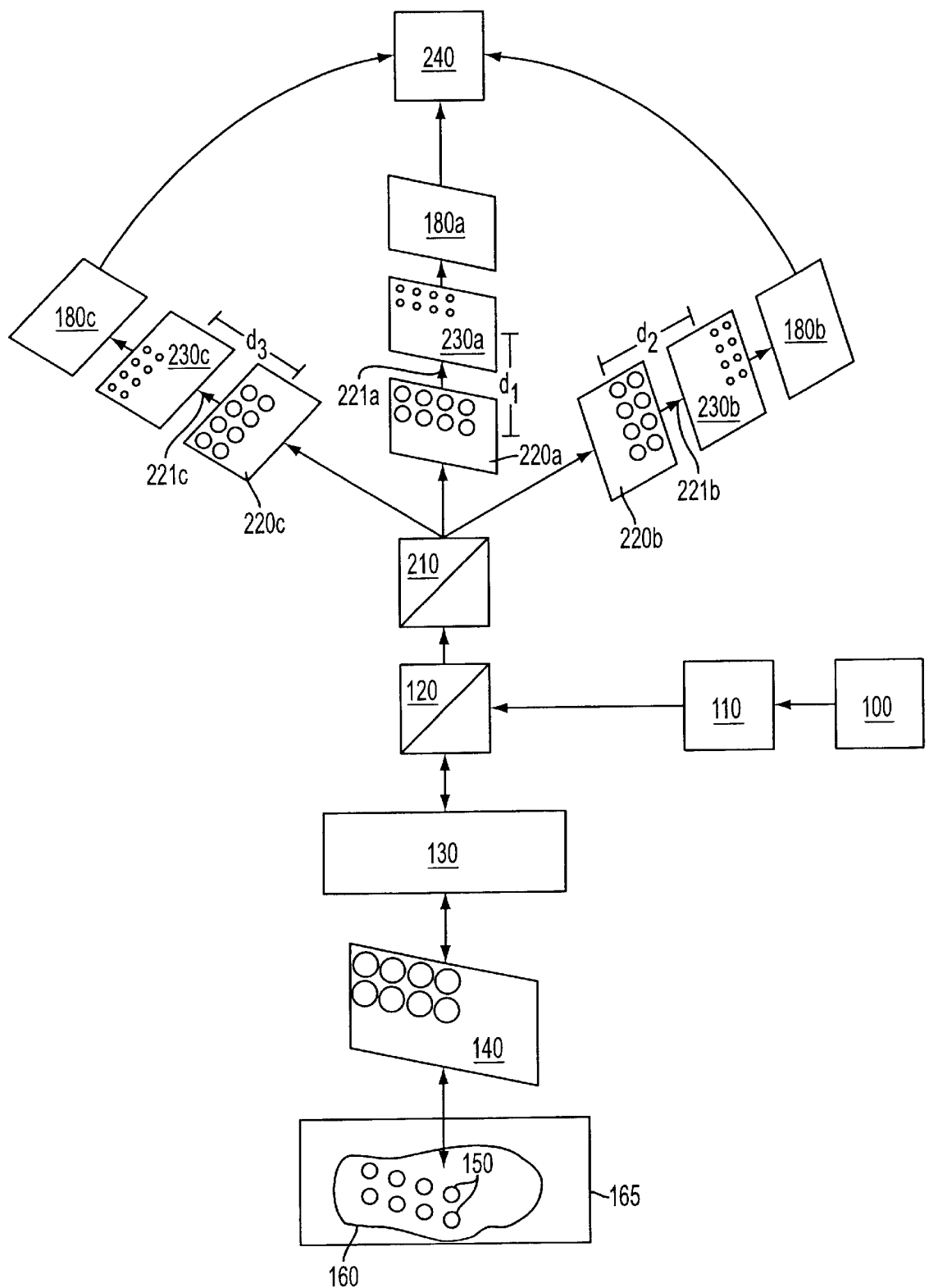
Figure 1G:
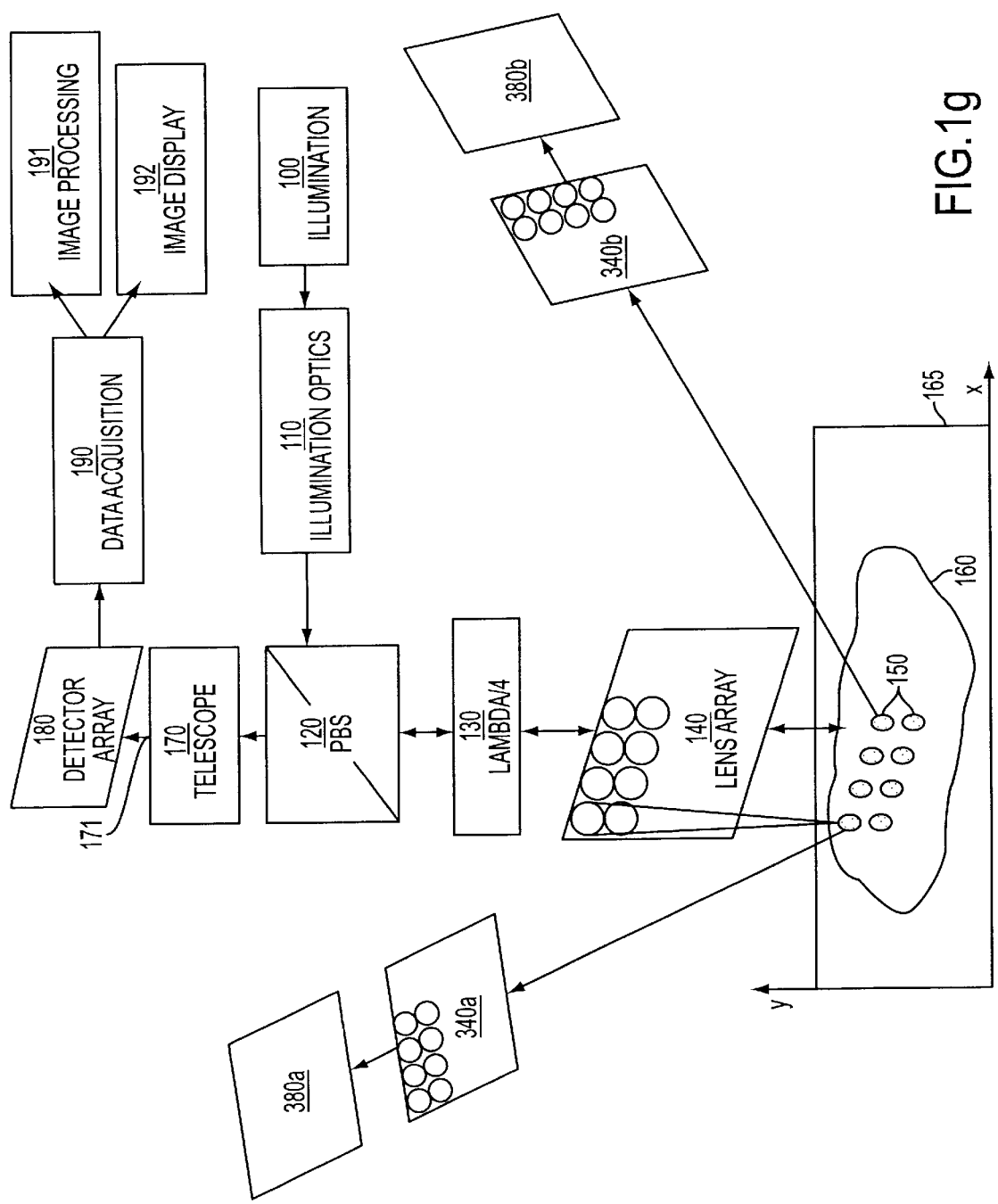
Figure 1H:
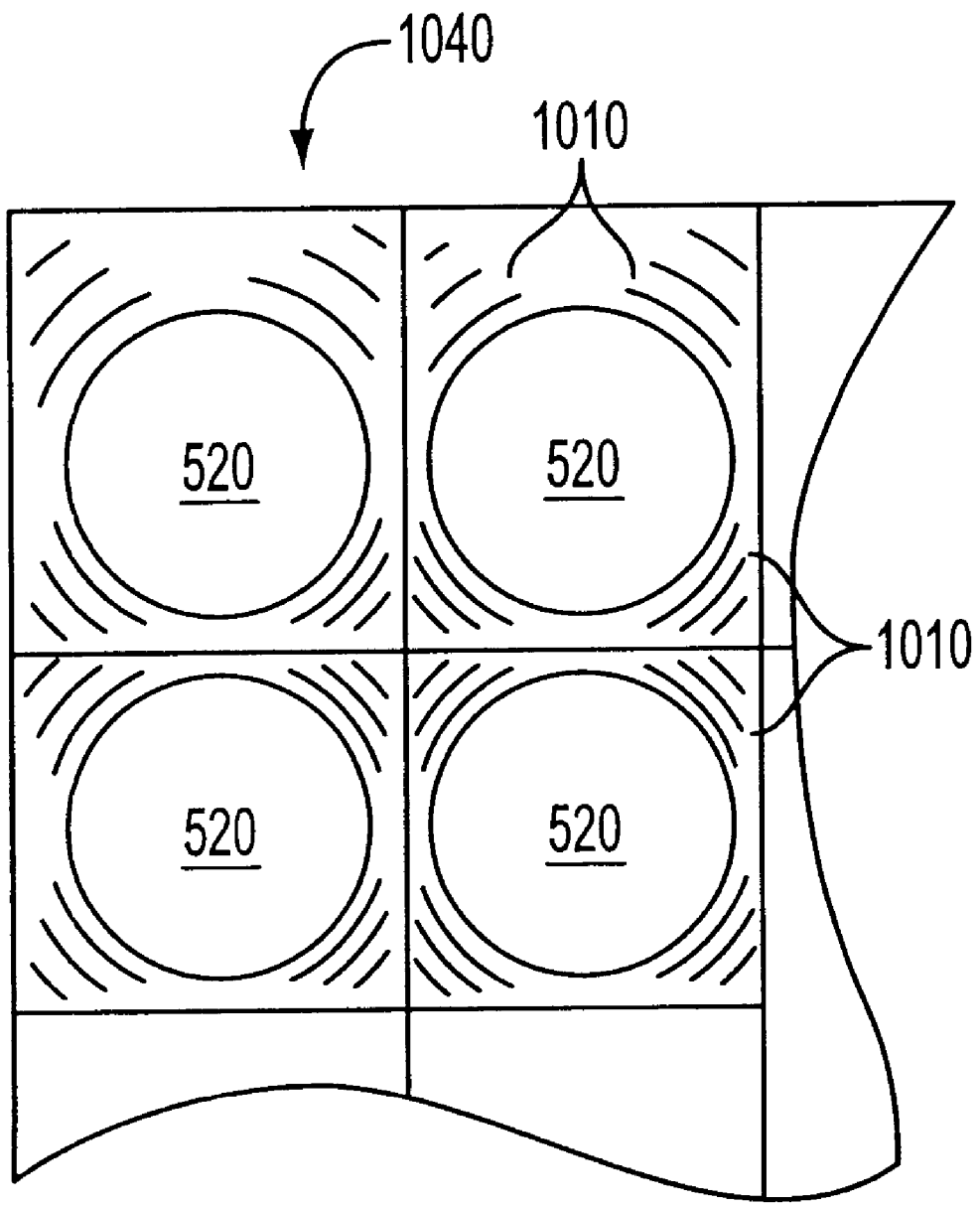
Figure 1I:
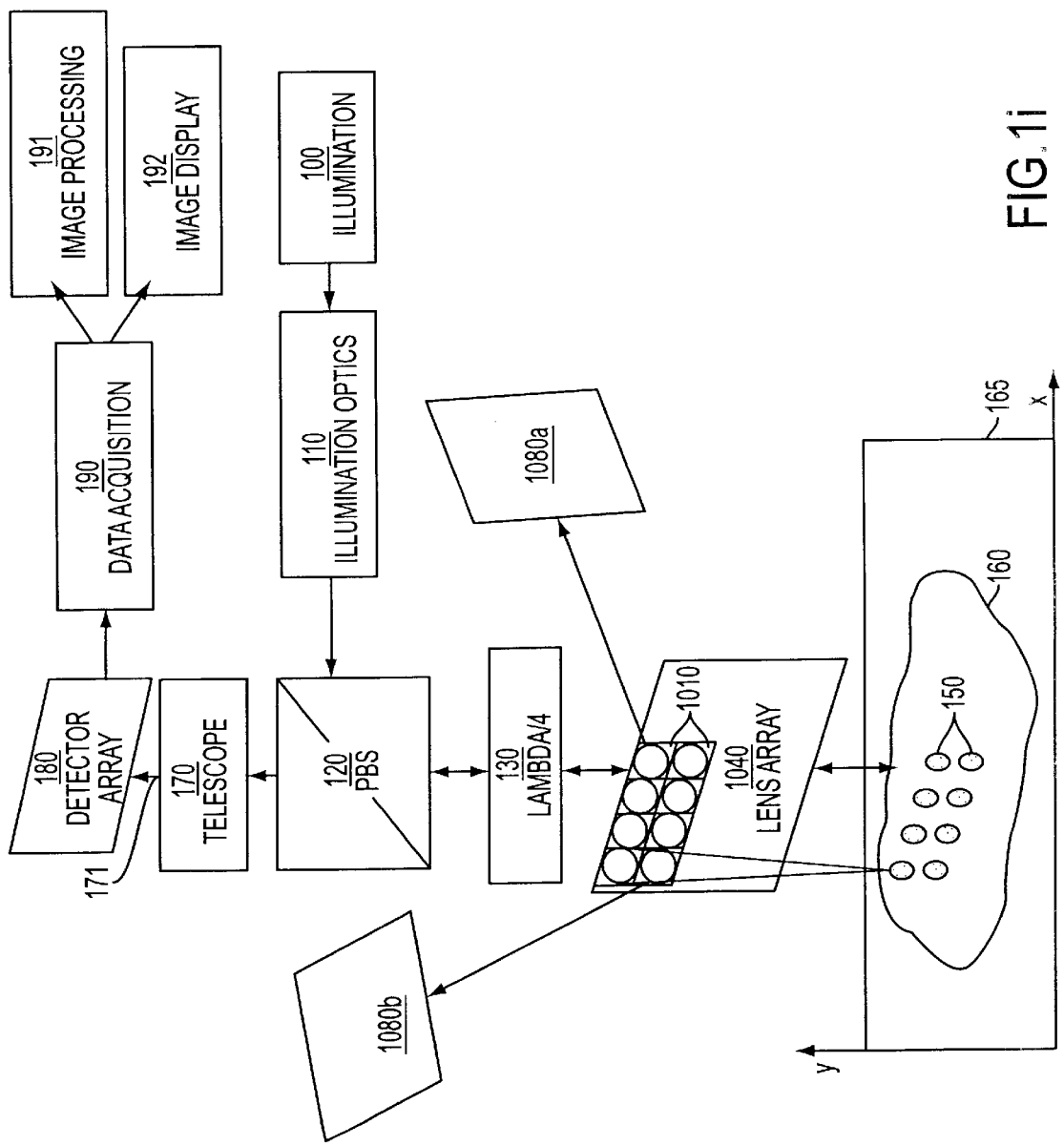
Figure 1J:
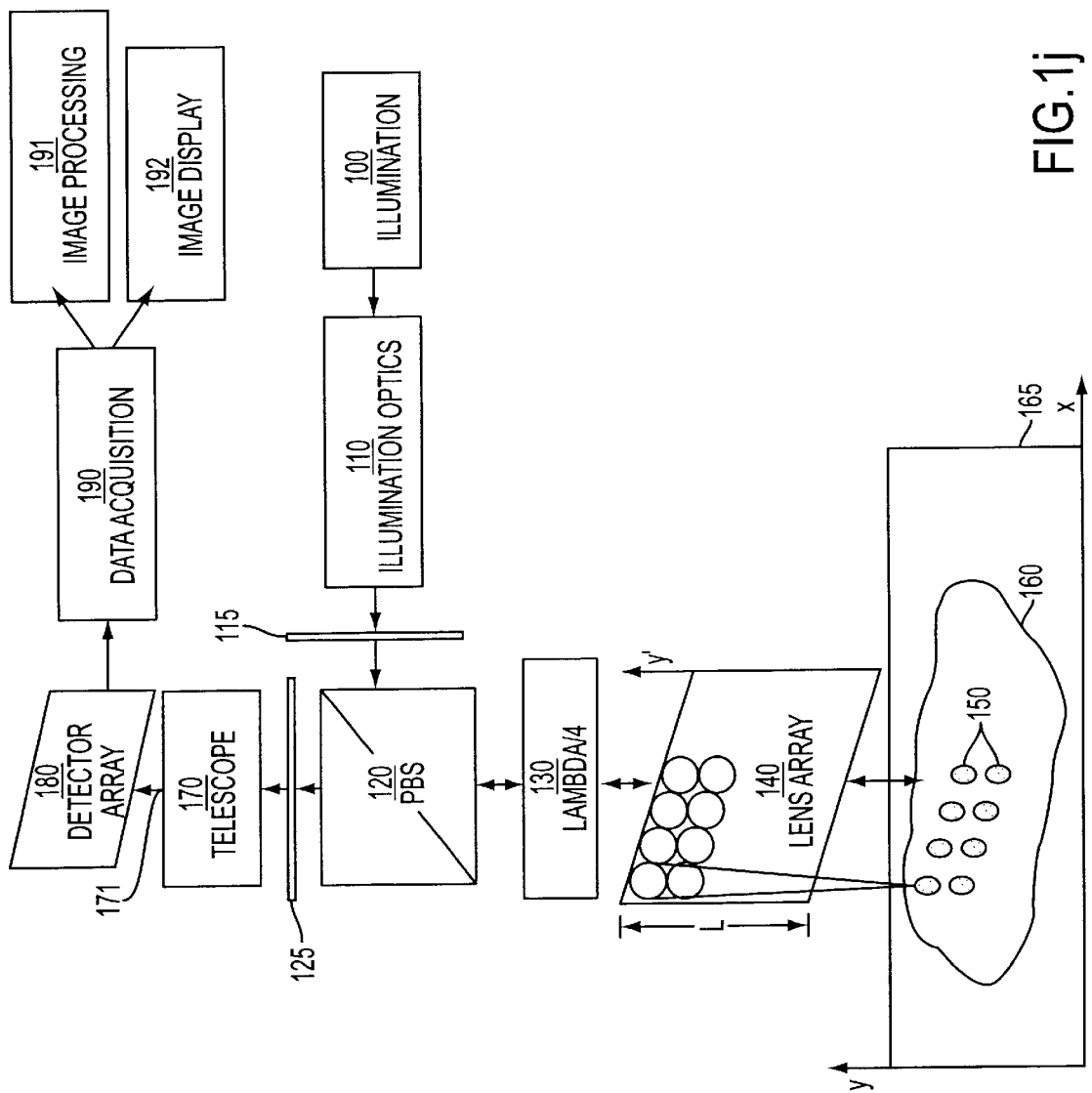
Figure 1K:
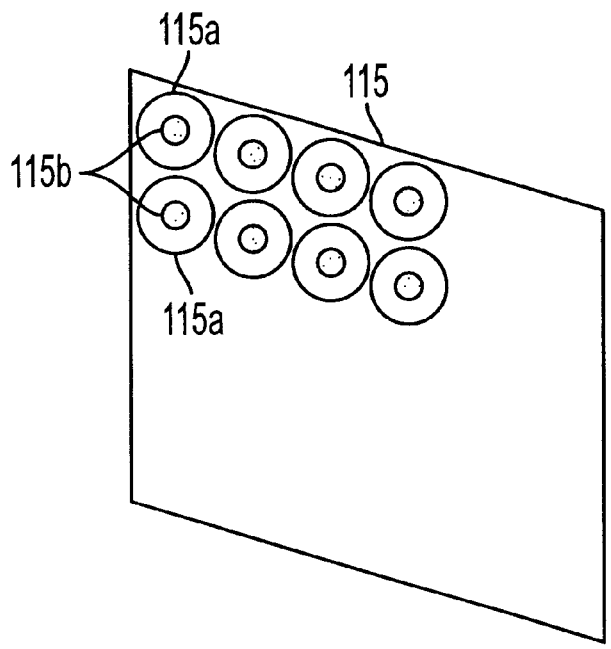
Figure 1L:
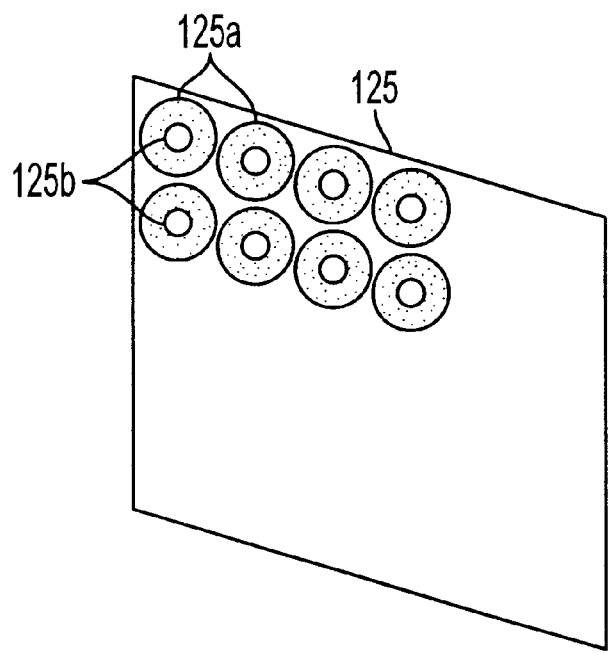

In a further embodiment of the present invention illustrated in FIGS. 1j–l, the back pupils of the lenses in array 140 are not identical for the illumination path and the collection path. This difference is achieved by placing an aperture either in the illumination path or in the collection path or in both. For example, by blocking the pupil centers in the illumination path and allowing only those centers through in the collection path we get a darkfield microscope. This blocking of the center of each lens allows finer resolution. The cost is stronger side-lobes, but these can be accommodated if a large lens array is used (e.g., 320×320 vs. 32×32).

Referring now to FIG. 1j, a darkfield microscope according to this embodiment of the present invention is obtained by placing a plane 115 in the illumination path between illumination optics 110 and beam splitter 120 of FIG. 1a. As shown in FIG. 1k, plane 115 has dark circles 115b blocking the light in the center of individual circular apertures 115a corresponding to lens array 140, thereby resulting in a ring aperture. Another plane 125, as shown in FIGS. 1j and 1l, is placed between beam splitter 120 and telescope 170, and is the reverse of plane 115; i.e., the center 125b of each element 125a is transparent, and the remainder opaque, resulting in a central circular aperture. Alternatively, planes 115 and 125 can be switched (i.e., central circular apertures in the illumination path and ring apertures in the collection path), and the darkfield microscope of this embodiment of the present invention will nevertheless result.

For high resolution imaging, it is desirable to create spot array 150 using lenses with a large numerical aperture; e.g., about 0.8. However, micro-lenses typically have a numerical aperture of about 0.4 or less. In a still further embodiment of the present invention illustrated in FIG. 1b, micro-lens array 140a employing inexpensive and readily available micro-lenses with low numerical apertures (e.g., about 0.1) is used to create a relatively large array of spots in an intermediate plane IP, which array is then de-magnified to the desired spot array size and projected by conventional optics 145 (called "a relay optical system" or "relay optics") upon substrate 160. This embodiment allows the use of inexpensive micro-lenses, thereby lowering the cost of the imaging system.

The use of microlens technology results in a relatively flat optical surface that is in close proximity (typically several tens of microns or even less) with the substrate. Referring again to FIG. 1a, in one embodiment of the present invention, the gap between lens array 140 and substrate 160 is filled with a liquid having an optimized refractive index; e.g., an index of refraction larger than that of air (n>1) which leads to improved resolution. Whereas a large NA and large FOV lens would have a large curvature requiring a substantial liquid media, the use of an array of lenses allows for a much lower volume of liquid. This embodiment of the present invention provides the advantage of immersion microscopy of effectively shortening of the optical wavelength, hence obtaining a finer resolution limit. A further advantage of large FOV immersion microscopy is the ability to do inspection of substrates processed in a liquid environment before their drying, such as in chemical mechanical polishing (CMP).

In an alternative embodiment of the present invention, illustrated in FIG. 1c, an array of lasers 100a, each laser individually controlled, is used as the light source to create a spot array on substrate 160. Laser array 100a can comprise an array of vertical cavity surface emitting lasers (VCSELs), available from Band Gap Engineering of Colorado. VCSELs are semiconductor lasers that emit light from the top of the chip, straight up. Light from laser array 100a is passed through a lens 120a to illuminate substrate 160. Beam splitter 120a is placed in a conjugate plane of light reflected from substrate 160, so light from laser array 100a passes through the conjugate plane, and reflected light from substrate 160 is directed to detector array 180, as shown in FIG. 1c. Thus, a lens array is not needed in this embodiment of the present invention.

The present methodology is compatible with photo-electron emission microscopy (PEEM). In a PEEM implementation, the system illuminates spots on a substrate (e.g., spots 150 on substrate 160) and collects emitted electrons to perform electron rather than photon (optical) imaging. Thus, detector array 180 comprises conventional sensors for detecting photo-electron emissions, such as a multi-channel plate (MCP) coupled to a CCD detector array, or a scintillator coupled to a CCD or MCP. Use of the present invention's discrete spot illumination with well separated spots enables high resolution PEEM with low resolution requirements for the electron imaging system, which only needs to provide sufficient resolution to prevent cross-talk between the separate spots.

The present invention also enables fast and efficient confocal imaging with continuous stage motion. In a further embodiment of the present invention, an array of pin-holes of the desired size and with separation corresponding to the micro-lens array is placed in a conjugate image plane and adjusted so the pinholes are concentric with the individual spot elements. Referring now to FIG. 1e, microlens array 141 is used as the focusing optics to generate the conjugate image plane 141a, and pinhole array 142 is placed in conjugate image plane 141a concentric with the microlenses of lens array 141. This technique is advantageous over prior art confocal imaging systems because there are no pin-holes in the illumination path and all of the source brightness is used. Moreover, this technique is compatible with laser as well as white-light illumination. Furthermore, the elements of microlens array 141 can be inexpensive diffractive microlenses, and the pinholes of pinhole array 142 can be advantageously sized to allow only the center spot generated by the diffractive microlenses pass to detector array 180, while blocking out undesirable side bands.

In a further embodiment of the present invention, illustrated in FIG. 1f, one or more conventional beam-splitting elements 210 are inserted in the collection path to split the conjugate plane of lens array 140 back pupil. Focusing optics 220a–c, such as a microlens array similar to lens array 140, is inserted for each conjugate pupil plane to form multiple conjugate image planes 221a–c. For each conjugate image plane 221a–c, a pin-hole array 230a–c is placed with a different lateral shift relative to the best focus plane; that is, the distance d1 between lens array 220a and pin hole array 230a is different than the distance d2 between lens array 220b and pin hole array 230b, and the distance d3 between lens array 220c and pin hole array 230c is different than distance d1 or d2. By placing an imaging array (CCD) 180a–c after each pin-hole array 230a–c, multiple images are simultaneously generated, each of a different height slice on substrate 160. In this way, the multiple imaging arrays 180a–c can be used to simultaneously inspect the same spot on substrate 160 from different heights. The data from the multiple arrays 180a–c can then be resampled to generate the image of the best focus plane. For example, gray level information for a given pixel on the surface of substrate 160 from each of the arrays 180a–c can be processed by signal processor 240 to compensate for imperfect focus tracking.

In yet another embodiment of the present invention, reflected light from the spots formed on the substrate is collected from several directions simultaneously. This multi-perspective imaging technique enables defect detection and classification to be conducted with greater accuracy, since certain types of defects reflect light in characteristic known directions. Thus, the presence or absence of reflected light at a particular angle in relation to the substrate can be used to determine the presence of a particular type of defect.

The multi-perspective imaging of this embodiment of the present invention can be achieved by placing several optical systems, such as microlens arrays 340a, 340b, and associated detector arrays 380a, 380b at different angles with relation to substrate 160, as depicted in FIG. 1g. Instead of lens arrays 340a, 340b, any conventional optical systems can be employed that are capable of imaging the entire field of view of substrate 160 with the resolution of the separation of spots 150. Alternatively, as illustrated in FIG. 1h, a single lens array 1040 is provided comprising diffractive elements 1010, such as in the spaces between lenses 1020. Diffractive elements 1010 divert light scattered at different angles from substrate 160 to either particular regions of detector array 180 or to several detector arrays 180, 1080a, 1080b, as shown in FIG. 1i.

In the embodiment of FIGS. 1a and 2, the shift in the mechanical cross-scan x direction between the lens centers of lenses in consecutive lines determines the pixel size in the x direction (e.g. the projection $p_x$ on the x-axis of the distance between the e'th lens in the first line e1 and the e'th lens in the 2nd line e2). Moreover, the last spot in one column (d6) passes a distance of one cross-scan pixel ($p_x$) away from the path of the spot created by the first lens in an adjacent column (c1). Therefore, the distance between the lens columns or the lens pitch determines the number of lens rows in the array ($n_r$).

Figure 3B:
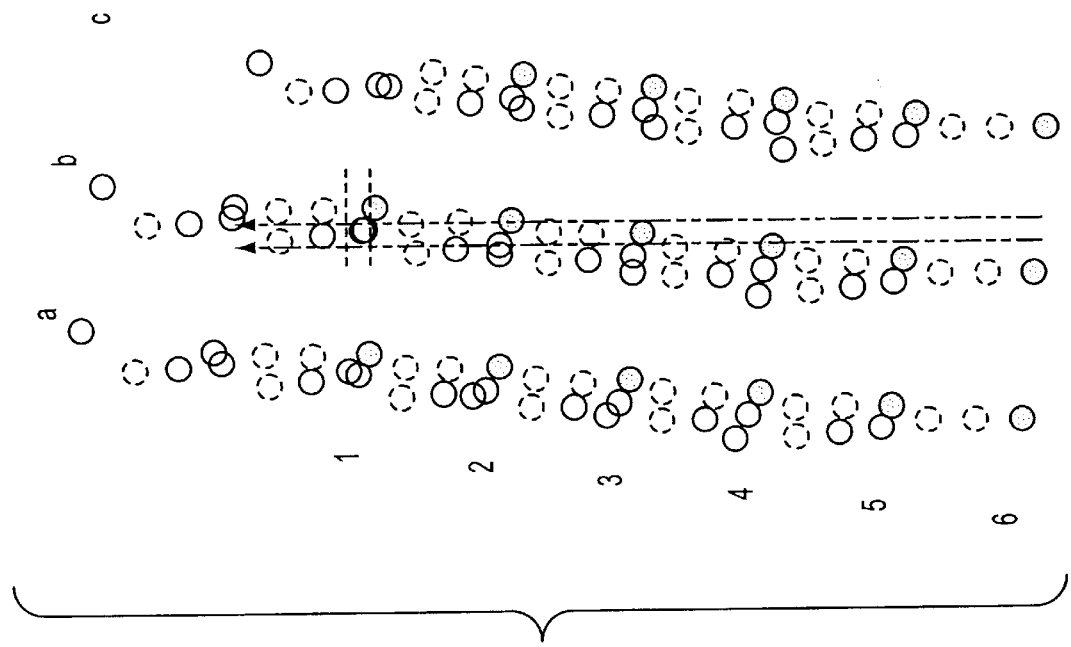
FIGS. 3a and 3b depict spot arrays according to embodiments of the present invention.
Figure 3A:
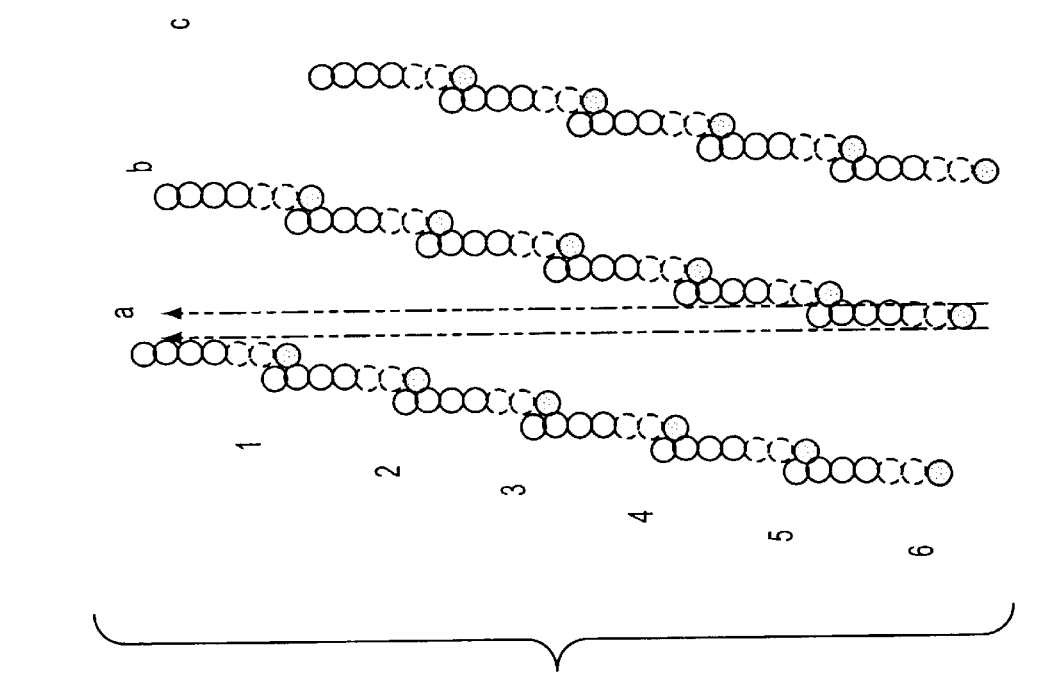

In an alternative embodiment of the present invention, a larger number of rows ($n_r$) are used, and the array is tilted such that the x-axis separation between the paths of lens in consecutive rows is a fraction (f) of the pixel-size ($p_x/f$). The substrate velocity is chosen such that it transverses a distance in the y-axis a factor f larger than a single pixel ($p_y/f$). Referring now to FIG. 3a, wherein a simple scan pattern is shown, for a given pixel created by lens $b1_1$, the subscript stands for the writing period, the y neighbor on top is $b1_2$, and the x neighbor on the left is $b3_n$ where $n=s/p_y$ (to create a rectangular array, the value of $s/p_y$ needs to be an integer). In FIG. 3b, however, an interlace scanning pattern is created (it shows f=2 for simplicity). In this case, $b1_1$ and $b1_2$ will be separated by a distance of $2p_y$, where the adjacent pixel to $b1_1$ will be $b2_n$, and $n=s/2p_y$. $b1_2$ will be shifted relative to $b1_1$ in a diagonal with a slant of 1/f. Therefore, for a large f the separation is mainly in the y direction. The result is a continuous coverage of the substrate achieved by an interleaving of f periodic structures offset in both axes.

An advantage of the interleaving of this embodiment of the present invention is a larger number of individual spots in a given FOV. Therefore for an identical pixel-rate requirement the array read rate ("frame-rate") can be lower since there are more elements in the array. When practicing this embodiment, close tolerances on the linearity of the motion of the mechanical stage and on the inter-lens spacing are necessary. Furthermore, the light source must be in the form of short pulses, rather than continuous waves (CW).

To obtain good results when practicing the spot array concept of the present invention, close tolerances on the linearity of the optics is important—both for the microlens array and for the de-magnification optical elements. The optical spots must be located on an exactly rectilinear grid with very exact distances between the spots. For example, if we have a grid 1000 rows deep, the thousandth row spot of column n must pass accurately near the location which was viewed by the first row's spot of column n−1. Assuming a desired accuracy of $1/10^{th}$ of a pixel, this implies linearity of one tenth of a pixel over the length of the FOV. Where the lens pitch is equal to 100 pixels, the linearity requirement is therefore $1:10^6$ (1000 rows * 100 pixels pitch/0.1 pixel tolerance=$10^6$). This requirement for extreme accuracy is problematic if mechanical vibrations are present.

In a further embodiment of the present invention, this severe linearity requirement is removed by creating a small overlap between the coverage areas of the lenses in consecutive columns, thereby reducing the deleterious effects of mechanical vibration on the system. This is achieved by providing additional rows of lenses; e.g., adding rows "7" and "8" in the spot array of FIG. 2. Furthermore, in most automated inspection systems, such as Applied Materials' WF-736, the image comparison is done between two locations along the substrate scanning direction. The additional rows of pixels of this embodiment enable pixels generated by individual columns to be compared to pixels generated by the same column. Moreover, image processing algorithms typically require operations on a given pixel's neighbor. The overlap between columns (i.e., the additional rows of pixels) is preferably sufficient to provide "spare" pixels (typically 1 to 5 pixels) to ensure that neighboring pixels used for purposes of an algorithm are all from the same column. In this way, spot d6 does not have to be compared with a remote spot such as c1. This embodiment essentially makes the lenses of each column into an individual data-path. It is also compatible with the use of a modularized image processing approach; for example, each column feeding into a separate image processing module. Such a modularized approach simplifies and speeds processing.

In this embodiment of the present invention, the linearity requirement is reduced to the distance between rows of an individual column which pass in the vicinity of each other. In the non-interlaced basic approach this distance is one lens pitch. For the case described above this is a linearity requirement of 1:1000 (100 pixels pitch/0.1 pixel tolerance). If interlacing is used (see FIG. 3b) the linearity requirement is multiplied by the interlace factor and thus becomes 1:10,000 for an interlace factor of 10.

As discussed above, a limitation of the prior art is the need to work with a coherent laser source to achieve sufficient power density for high-speed inspection. Many inspected substrates are covered by transparent or semi-transparent dielectric layers which cause interference phenomena between the surfaces of the dielectric layers. As the thickness of these layers varies across the wafer, the phase of the reflections from the top and bottom of each dielectric layer varies, and the resulting interference can be either constructive or destructive. This causes a change in the reflected power despite the absence of defects or irregularities, thereby limiting the capability of the system to identify true defects. To overcome this limitation of laser sources, some prior art inspection systems use broadband lamp illumination, which causes the effects of constructive and destructive interference to average out, rendering reflection intensity less dependent on dielectric layer thickness fluctuations.

However, lamp sources do not have the brightness of lasers, and this fact results in problems when the light from the lamp source is collimated prior to reaching the lens array. The more collimated the light at the lens array, the lower the available power. Low power requires a relatively long integration time to achieve a reasonable signal-to-noise ratio, and thereby limits the system's throughput. On the other hand, if the light is not collimated, the lens will not focus it to a diffraction-limited spot. A large illumination spot will either degrade the system's resolution or require a means in the collection optics, such as a pinhole array, to block out a portion of the large light spot and again create a weak signal requiring longer integration time and hence reduced throughput. Thus, prior art broadband lamp illumination schemes do not deliver adequate performance for spot grid array inspection systems.

Figure 4:
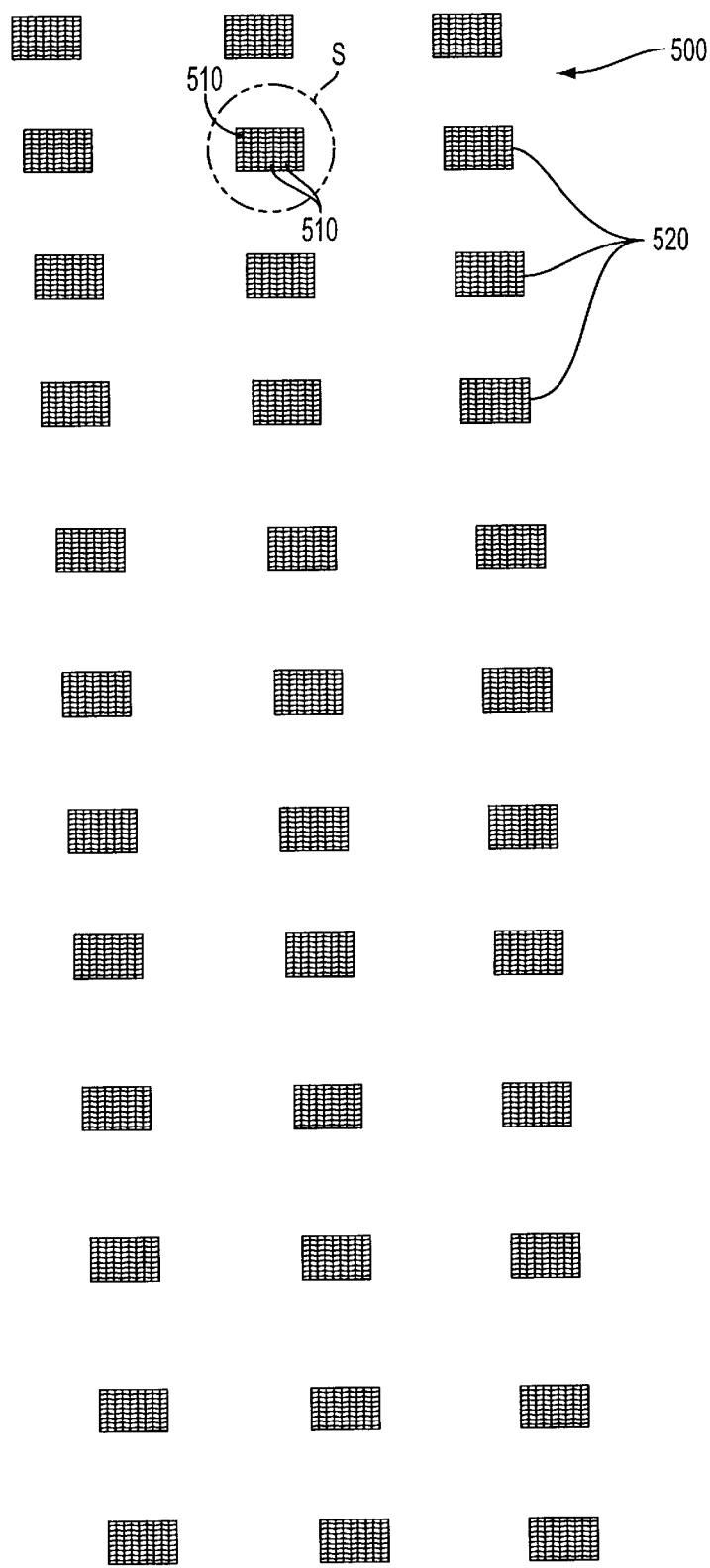
FIG. 4 schematically illustrates an imaging system in accordance with an embodiment of the present invention utilizing a broadband illumination system.

FIG. 4 illustrates an embodiment of the present invention that overcomes the above-discussed limitations of prior art broadband illumination systems. In this embodiment, partially collimated broadband light from a lamp source enabling sufficient illumination of the substrate is used, creating illumination spots S which are larger than the diffraction limit. The imaging CCD array 500 shown in FIG. 4 is designed with pixel sizes corresponding to the system's required resolution. Each illumination spot S is thus imaged on more than one pixel 510 at a time.

As the substrate moves beneath the lens array 500 of this embodiment (e.g., along the y-axis), the same substrate location is imaged by corresponding pixels 510 of detector array 500 as the substrate location is illuminated by different parts of illumination spot S. The signal from the rows of pixels 510 is added "in sync" with the motion of the substrate, thus adding together the signals generated by different parts of illumination spot S. This embodiment of the present invention can be implemented either by charge transfer on a conventional CCD array, or by any well-known analog or digital technique, either on or off the detector array chip.

Furthermore, the signal corresponding to the same location on the substrate generated by the following lens and collected on other pixels 510 in detector array 500 can also be added to the signal from the previous lens. The example in FIG. 4 shows an integration of pixels from 10 consecutive rows for one lens' spot and an integration of 10 lenses—overall an integration of 100 pixels. This 100-fold improvement in the effective brightness of the illumination source enables the use of a lamp source rather than a laser for overcoming the interference issues discussed above, while providing adequate throughput.

The detector array of this embodiment can be a uniform grid. In this case, only some portions of it would be utilized. Alternatively, it can be composed of a dense array for each lens, separated by an area that can be used for supporting electronics. For the example illustrated in FIG. 4, we have a 10 by 10 pixel sub-array 520 for each lens, with a pitch equal to 100 by 100 pixels. Detector array 500 is tilted at the same angle as in the previously described embodiments to ensure full substrate coverage as well as integration of the signal from the sequential lenses illuminating a given area. Use of broadband illumination, as in this embodiment of the present invention, requires the use of refractive and not diffractive lens elements, as the latter's focal length is linearly dependent on wavelength.

Figure 5:
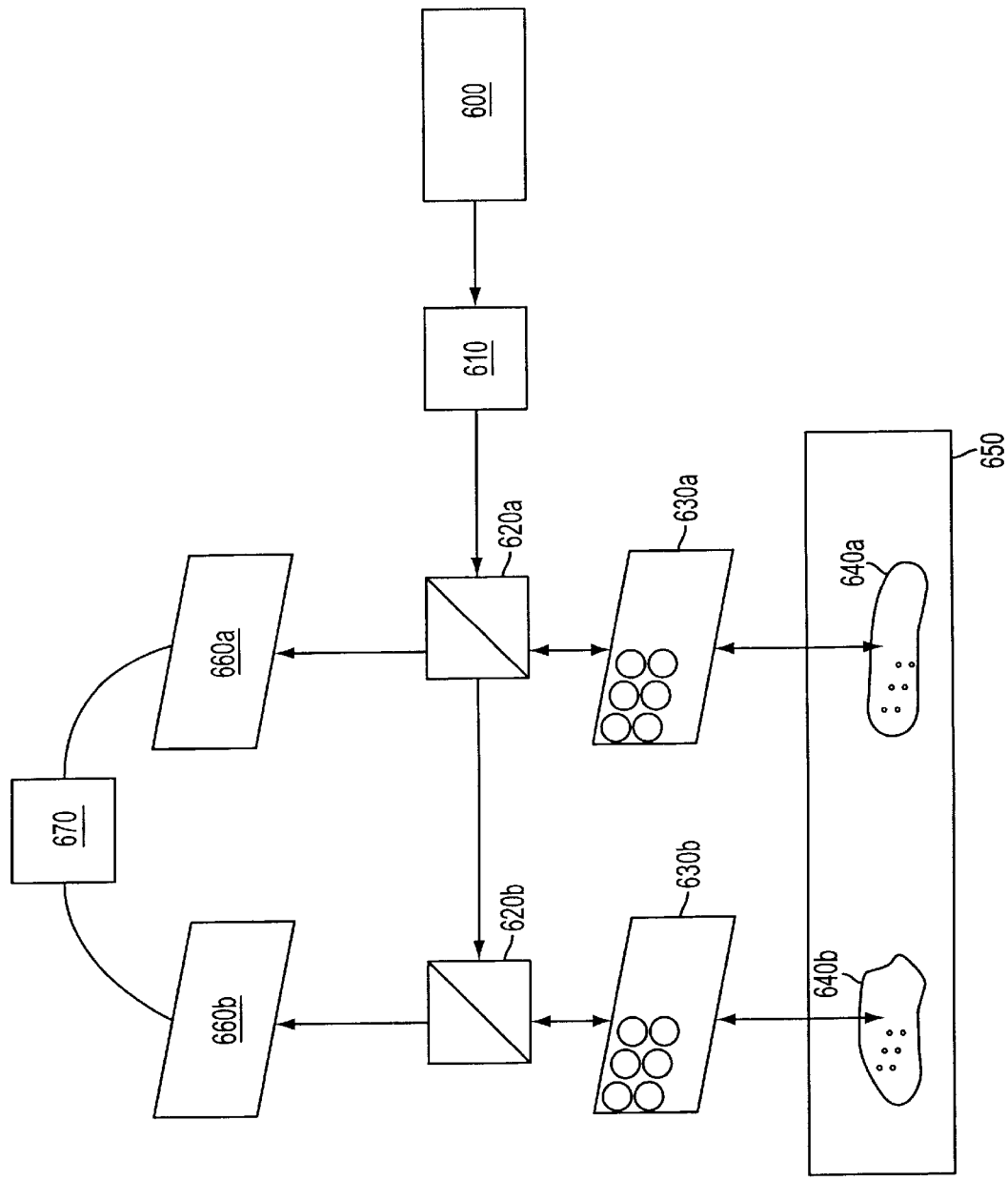
FIG. 5 schematically illustrates an imaging system in accordance with an embodiment of the present invention wherein two substrates are imaged simultaneously.

In a further embodiment of the present invention illustrated in FIG. 5, two corresponding substrates 640*a*, 640*b*, such as two identical dies from the same wafer, are placed on a movable stage 650, and one die is used as a reference for inspection of the other die. A radiation source 600, which can be any one of the illumination sources described above, provides light that impinges upon lens arrays 630*a*, 630*b*, as through illumination optics 610 and beam splitters 620*a*, 620*b* as necessary, to irradiate identical arrays of spots on substrates 640*a* and 640*b*. Lens arrays 630*a*, 630*b* can be any of the arrays discussed above.

Signals from substrates 640*a* and 640*b* are collected by detector arrays 660*a*, 660*b*, and the resulting images compared by processor 670 to determine if defects exist on one of the substrates 640*a*, 640*b*. For example, the gray levels of corresponding pixels of the two images are compared, and if they differ by more than a predetermined threshold amount, processor 670 determines that a defect exists at that pixel location. As in previous embodiments of the present invention, movable stage 650 moves such that substantially the entire surface of each substrate 640*a*, 640*b* is irradiated and imaged. However, an advantage of this embodiment of the present invention is that since both substrates 640*a*, 640*b* undergo the same vibrations of stage 650, the unwanted effects of that vibration are not relevant, and do not need to be compensated for, as they do in the other embodiments described herein.

The following examples illustrate the calculation of various parameters relevant to the practice of the present invention:

Definitions

FOV—Field-of-view in microns on substrate (assume square)

D—Pitch between spots on substrate in microns p—Pixel size on substrate in microns $n_y$ and $n_x$—number of rows and columns in array respectively N—total number of lens in array DR—Data-rate requirement (pixels/second/array)

FR—Frame-rate requirement (array-read/second)

V—stage velocity in y direction in microns/sec

Since FOV=D * $n_x$, $n_y$=D/p. Thus, the total number of lenses N is calculated by:

$$N = n_x * n_y = (FOV/D) * (D/p) = FOV/p$$

For a given data-rate requirement (DR) the frame rate (FR) and hence stage velocity required are:

$$FR = DR/N = DR*p/FOV$$

and $$V = FR*p = DR*p^2/FOV$$

EXAMPLE 1

FOV=1 mm=1000 micron

DR=10 Giga-pix/sec=$10^{10}$ pix/sec

P=100 nm=0.1 micron

⇒N=1000/0.1=10,000=$10^4$ => an 100 by 100 array;

⇒FR=$10^{10}/10^4=10^6$=1 mega-frames/second

⇒V=$10^6$*0.1 micron=100 mm/sec

For a given pixel size, increasing the FOV is key to obtaining a larger number of pixels in the array, and hence to reduced frame-rates and stage velocity requirements (when using interleaving as shown in FIG. 3*b*, the number of rows and hence array elements increases and the frame-rate goes down, but the stage velocity requirement remains unchanged). In the embodiments of the present invention employing direct lens array to substrate imaging, the FOV is not a limitation. However, when using conventional optics to re-image the microlens array upon the substrate, FOV becomes an issue.

EXAMPLE 2

If the pixel size is reduced to 10 nm and the FOV is increased to 10 mm, the total number of array spots is N=10,000/0.01=$10^6$. Keeping the frame-rate (FR) at $10^6$ frames/second, the data rate (DR) of the present invention becomes $10^{12}$ pixels/second or one Tera-pixels/second. The stage velocity (V) at this DR is 10 mm/sec. This system according to the present invention is three orders of magnitude faster than any prior art system. Of course, such a system requires conventional image acquisition and image processing systems capable of handling a high data-rate. For example, the resolution of the system according to this embodiment of the present invention can be obtained with EUV (Extended UV with a wavelength ~13–14 nm) optics.

The present invention can be practiced by employing conventional materials, methodology and equipment.

Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An imager comprising:
    a radiation source for simultaneously irradiating an array of spots spaced apart from each other on a surface of an object to be imaged;
    a detector array for collecting signals resulting from an interaction of the spots with the surface of the object to form an image of the irradiated portions of the object surface;
    a movable stage for supporting the object and moving the object such that a predetermined portion of the surface of the object can be irradiated and imaged; and
    a compensator for compensating for mechanical inaccuracies in the movable stage.

2. The imager of claim 1, wherein the radiation source comprises:
    a light source; and
    an array of lenses for focusing light from the light source into the array of spots on the surface of the object.

3. The imager of claim 2, wherein the lenses are micro-lenses.

4. The imager of claim 3, wherein the micro-lenses are diffractive or refractive.

5. The imager of claim 3, wherein the light source is a laser, and the imager comprises illumination optics for collimating and directing laser light from the light source through the micro-lens array to impinge on the object surface.

6. The imager of claim 5, wherein the illumination optics comprises a beam splitter to direct the collimated laser light to the micro-lens array, wherein the beam splitter is for allowing the light reflected from the spots to pass through to the detector array.

7. The imager of claim 5, wherein the illumination optics comprises a polarizing beam splitter to direct the collimated laser light to the micro-lens array, and a quarter-wave plate between the beam splitter and the micro-lens array for polarizing the laser light, wherein the beam splitter and the quarter-wave plate are for allowing the light reflected from the spots to pass through to the detector array.

8. The imager of claim 2, wherein the light reflected from the spots forms an intermediate image having a size substantially equal to the size of the lens array, the imager comprising a telescope between the lens array and the detector array for demagnifying the intermediate image.

9. The imager of claim 2, further comprising a relay optical system between the lens array and the object for demagnifying the array of spots.

10. The imager of claim 1, wherein the movable stage is for moving the object substantially linearly in a scanning direction that deviates from an axis of the spot array such that as the object is moved a distance substantially equal to a length of the spot array in the scanning direction, the spots trace a substantially continuous path on the object surface in a mechanical cross-scan direction.

11. The imager of claim 1, wherein the detector array comprises a CCD.

12. The imager of claim 2, wherein the light source is for supplying light in the extreme ultraviolet range.

13. The imager of claim 2, wherein the detector array is for detecting photo-electron emissions.

14. The imager of claim 2, wherein the lens array is two-dimensional, and the detector array is two-dimensional and corresponds to the lens array.

15. The imager of claim 2, wherein the light source is a continuous light source.

16. The imager of claim 2, wherein the light source is a pulsed light source.

17. The imager of claim 1, wherein the compensator comprises a servo for moving the spot array to compensate for the mechanical inaccuracies.

18. The imager of claim 2, wherein the compensator is selected from the group consisting of a movable mirror, an electro-optic element and an acousto-optic element for varying an angle of incidence of the light source onto the surface of the object for compensating for the mechanical inaccuracies in the movable stage.

19. The imager of claim 8, wherein the telescope is a confocal telescope.

20. The imager of claim 2, further comprising a fluid having a substantially optimized refractive index disposed in and filling a gap between the lens array and the object.

21. The imager of claim 3, further comprising a member having an array of pinholes corresponding to the lenses of the micro-lens array, the member being disposed in a conjugate image plane between the object and the detector array such that the pinholes are concentric with the spots of the spot array.

22. The imager of claim 21, further comprising a second array of micro-lenses for generating the conjugate image plane.

23. The imager of claim 3, further comprising:
    a beam splitter disposed between the micro-lens array and the detector array to split a conjugate plane of a back pupil of the micro-lens array into a plurality of conjugate pupil planes;
    focusing optics associated with each conjugate pupil plane for forming a conjugate image plane for each pupil plane;
    a plurality of members, each member having a pin-hole array and associated with one of the image planes, each member disposed such that it has a different lateral shift; and
    a plurality of detector arrays, each detector array associated with one of the members for receiving light from the pin hole array, wherein the detector arrays are for simultaneously generating a plurality of images of the object.

24. The imager of claim 10, wherein the movable stage is for moving the object such that the spots overlap as they trace the continuous path on the object surface.

25. The imager of claim 24, wherein the movable stage is for moving the object such that the spots are interleaved as they trace the continuous path on the object surface.

26. The imager of claim 24, wherein the spot array comprises a plurality of rows and columns of spots, and the radiation source is for irradiating a predetermined number of rows of spots such that the spots of two adjacent ones of the columns overlap as they trace the continuous path on the object surface.

27. The imager of claim 1, wherein the radiation source comprises an array of lasers directed at the object surface to form the spot array.

28. The imager of claim 27, further comprising a beam splitter for directing reflected light from the object to the detector array.

29. The imager of claim 2, wherein a first portion of the light from the light source is reflected from the array of spots at a first angle to the detector array, and a second portion of the light from the light source is reflected at a second angle different from the first angle, the imager further comprising a second detector array for collecting signals corresponding to the second portion of the light.

30. The imager of claim 29, comprising a second lens array between the spot array and the second detector.

31. The imager of claim 29, wherein the lens array comprises diffractive elements to divert the second portion of the light to the second detector array.

32. The imager of claim 2, wherein the lens array comprises rows and columns of lenses corresponding to the spot array, and the movable stage is for moving the object from a first position to a second position such that the spots on the object surface irradiated by the lens array at the second position overlap the spots on the object surface irradiated at the first position.

33. The imager of claim 2, wherein each lens of the lens array comprises a plurality of lenses in series.

34. The imager of claim 23, further comprising an image processor for processing the simultaneously generated images of the object to compensate for imperfect focussing.

35. The imager of claim 3, further comprising a member having an array of masks corresponding to the centers of the lenses of the micro-lens array, the member being disposed in a conjugate image plane between the object and the detector array such that the masks are concentric with the spots of the spot array.

36. The imager of claim 1, wherein the radiation source is for irradiating a first path between the radiation source and the surface of the object, and the detector array is for collecting the signals from the surface of the object along a second path different from the first path.

37. The imager of claim 36, wherein the radiation source comprises:
a light source; and
an array of lenses for focusing light from the light source into the array of spots on the surface of the object.

38. An imager comprising:
an illumination source comprising a broadband lamp, for simultaneously illuminating an array of spots spaced apart from each other on a surface of an object to be imaged;
a detector array for collecting signals resulting from the interaction of the spots with the surface of the object to form an image of the illuminated portions of the object surface, the detector array comprising a plurality of pixel arrays, each pixel array corresponding to one of the spots; and
a movable stage for supporting the object and moving the object such that a predetermined portion of the surface of the object can be illuminated and imaged;
wherein the illumination source is for illuminating the array of spots such that the signal from each spot is collected by more than one pixel of one of the pixel arrays at a time.

39. The imager of claim 38, wherein a portion of the surface of the object is imaged by a corresponding portion of one of the pixel arrays by a plurality of portions of one of the spots as the stage moves the object.

40. The imager of claim 38, wherein the pixels of the pixel arrays are sized to provide a predetermined resolution, and
wherein the illumination source is for illuminating the array of spots such that each spot is larger than a predetermined diffraction limit of the imager.

41. The imager of claim 38, wherein the detector array comprises a CCD.

42. An imager comprising:
a radiation source for simultaneously irradiating an array of spots spaced apart from each other on a surface of an object to be imaged;
a detector array for collecting signals resulting from the interaction of the spots with the surface of the object to form an image of the irradiated portions of the object surface; and
a movable stage for supporting the object and moving the object such that a predetermined portion of the surface of the object can be irradiated and imaged;
wherein the movable stage is for moving the object substantially linearly in a scanning direction that deviates from an axis of the spot array such that as the object is moved a distance substantially equal to a length of the spot array in the scanning direction, the spots trace a substantially continuous path on the object surface in a mechanical cross-scan direction; and
wherein the spot array comprises a plurality of rows and columns of spots, and the radiation source is for irradiating a predetermined number of rows of spots such that the spots of two adjacent ones of the columns overlap as they trace the substantially continuous path on the object surface.

43. The imager of claim 42, wherein the radiation source is for irradiating additional rows of spots, such that a total number of rows of spots is greater than the predetermined number of rows of spots, and the two adjacent ones of the columns overlap.

44. The imager of claim 43, wherein the radiation source is for irradiating a sufficient number of the additional rows of spots such that neighboring pixels used for an image processing algorithm are all from one of the columns.

45. The imager of claim 42, further comprising a compensator for compensating for mechanical inaccuracies in the movable stage.

46. An inspection system comprising:
a radiation source for simultaneously irradiating a first array of spots spaced apart from each other on a surface of a first object to be imaged and irradiating a second array of spots spaced apart from each other on a surface of a second object to be imaged, wherein the first and second spot arrays are substantially identical, and the surfaces of the first and second objects correspond to each other;
a first detector array for collecting signals resulting from the interaction of the spots with the surface of the first object to form an image of the irradiated portions of the first object surface;
a second detector array for collecting signals resulting from the interaction of the spots with the surface of the second object to form an image of the irradiated portions of the second object surface;

a movable stage for supporting the first and second objects and moving the objects such that substantially the entire surface of each object can be irradiated and imaged; and a processor for comparing the images of the first and second objects.

47. The inspection system of claim 46, wherein the processor is configured to determine whether a defect exists in the surface of the second object based on the comparison of the images of the first and second objects.

48. The inspection system of claim 47, wherein the processor is configured to determine that a defect exists in the surface of the second object when a value of a parameter of the image of the second object surface differs from a value of the parameter of the image of the first object surface by more than a predetermined threshold amount.

49. The imager of claim 46, further comprising a compensator for compensating for mechanical inaccuracies in the movable stage.

50. A method comprising the steps of:

simultaneously irradiating an array of spots spaced apart from each other on a surface of an object to be imaged;

collecting signals resulting from the interaction of the spots with the surface of the object to form an image of the irradiated portions of the object surface;

moving the object on a movable stage while the irradiating and collecting steps are being performed, such that a predetermined portion of the surface of the object can be irradiated and imaged; and compensating for mechanical inaccuracies in the movable stage.

51. The method of claim 50, comprising providing an array of lenses for focusing light from a light source into the array of spots on the surface of the object.

52. The method of claim 51, wherein the light reflected from the spots forms an intermediate image having a size substantially equal to the size of the lens array, further comprising demagnifying the intermediate image.

53. The method of claim 50, comprising moving the object substantially linearly in a scanning direction that deviates from an axis of the spot array such that as the object is moved a distance substantially equal to a length of the spot array in the scanning direction, the spots trace a substantially continuous path on the object surface in a mechanical cross-scan direction.

54. The method of claim 51, comprising irradiating the spot array using light in the extreme ultraviolet range.

55. The method of claim 51, comprising collecting photoelectron emissions.

56. The method of claim 51, comprising providing a fluid having a substantially optimized refractive index disposed in and filling a gap between the lens array and the object.

57. The method of claim 53, comprising moving the object such that the spots overlap as the trace the continuous path on the object surface.

58. The method of claim 57, comprising moving the object such that the spots are interleaved as they trace the continuous path on the object surface.

59. The method of claim 57, wherein the spot array comprises a plurality of rows and columns of spots, comprising irradiating a predetermined number of rows of spots such that the spots of two adjacent ones of the columns overlap as they trace the continuous path on the object surface.

60. The method of claim 51, further comprising:

reflecting a first portion of the light from the light source from the array of spots at a first angle to a first detector array for collecting signals corresponding to the first portion of the light; and reflecting a second portion of the light from the light source at a second angle different from the first angle to a second detector array for collecting signals corresponding to the second portion of the light.

61. A method comprising the steps of:

simultaneously irradiating an array of spots spaced apart from each other on a surface of an object to be imaged;

collecting signals resulting from the interaction of the spots with the surface of the object to form an image of the irradiated portions of the object surface;

focusing light from a light source into the array of spots on the surface of the object using an array of lenses;

placing a member having an array of pin-holes corresponding to the lenses of the array in a conjugate image plane between the object and the detector array such that the pinholes are concentric with the spots of the spot array; and moving the object on a movable stage such that a predetermined portion of the surface of the object can be irradiated and imaged.

62. The method of claim 61, comprising providing a second array of lenses for generating the conjugate image plane.

63. A method comprising the steps of:

simultaneously irradiating an array of spots spaced apart from each other on a surface of an object to be imaged;

focusing light from a light source into the array of spots on the surface of the object using an array of lenses;

collecting signals resulting from the interaction of the spots with the surface of the object to form an image of the irradiated portions of the object surface at a detector array;

splitting a conjugate plane of a back pupil of the lens array into a plurality of conjugate pupil planes;

forming a conjugate image plane for each pupil plane;

placing a plurality of members, each member having a pin-hole array and associated with one of the image planes, such that each member has a different lateral shift;

collecting signals resulting from the interaction of the spots with the surface of the object to simultaneously generate a plurality of images of the irradiated portions of the object, each image associated with one of the members for receiving light from the pin hole array;

moving the object on a movable stage such that a predetermined portion of the surface of the object can be irradiated and imaged; and compensating for mechanical inaccuracies in the moving stage.

64. A method comprising the steps of:

simultaneously irradiating an array of spots spaced apart from each other on a surface of an object to be imaged;

collecting signals resulting from the interaction of the spots with the surface of the object to form an image of the irradiated portions of the object surface;

focusing light from a light source into the array of spots on the surface of the object using an array of lenses;

placing a member having an array of masks corresponding to the centers of the lenses of the array in a conjugate image plane between the object and the detector array such that the masks are concentric with the spots of the spot array; and moving the object on a movable stage such that a predetermined portion of the surface of the object can be irradiated and imaged.

65. A method comprising:

simultaneously irradiating an array of spots spaced apart from each other on a surface of an object to be imaged;

collecting signals resulting from the interaction of the spots with the surface of the object to form an image of the irradiated portions of the object surface; and supporting the object and moving the object substantially linearly in a scanning direction that deviates from an axis of the spot array such that as the object is moved a distance substantially equal to a length of the spot array in the scanning direction, the spots trace a substantially continuous path on the object surface in a mechanical cross-scan direction, and a predetermined portion of the surface of the object is irradiated and imaged;

wherein the spot array comprises a plurality of rows and columns of spots, and the irradiating step comprises irradiating a predetermined number of rows of spots such that the spots of two adjacent ones of the columns overlap as they trace the continuous path on the object surface.

66. The method of claim 65, wherein the plurality of rows and columns of spots corresponds to an area of a portion of the surface of the object, the method comprising irradiating additional rows of spots, such that a total number of rows of spots is greater than the predetermined number of rows of spots, and the two adjacent ones of the columns overlap.

67. A method comprising:

simultaneously irradiating a first array of spots spaced apart from each other on a surface of a first object to be imaged and irradiating a second array of spots spaced apart from each other on a surface of a second object to be imaged, wherein the first and second spot arrays are substantially identical, and the surfaces of the first and second objects correspond to each other;

collecting signals resulting from the interaction of the spots with the surface of the first object to form an image of the irradiated portions of the first object surface;

collecting signals resulting from the interaction of the spots with the surface of the second object to form an image of the irradiated portions of the second object surface;

moving the first and second objects on a movable stage such that a predetermined portion of the surface of each object can be irradiated and imaged; and comparing the images of the first and second objects.

68. The method of claim 67, comprising determining whether a defect exists in the surface of the second object based on the comparison of the images of the first and second objects.

69. The method of claim 68, comprising determining that a defect exists in the surface of the second object when a value of a parameter of the image of the second object surface differs from a value of the parameter of the image of the first object surface by more than a predetermined threshold amount.

70. The method of claim 67, wherein the first and second objects are subject to substantially identical mechanical vibrations during the moving step.

71. The method of claim 67, comprising compensating for mechanical inaccuracies in the moving stage.

72. The method of claim 67, wherein the irradiating step comprises focusing light from a light source to form the first and second spot arrays.

73. The method of claim 67, wherein the irradiating step comprises directing laser light to impinge on the first and second surfaces to form the first and second spot arrays.

74. A method comprising the steps of:

simultaneously irradiating an array of spots spaced apart from each other on a surface of an object to be imaged;

collecting signals resulting from the interaction of the spots with the surface of the object to form an image of the irradiated portions of the object surface; and moving the object on a movable stage substantially linearly in a scanning direction that deviates from an axis of the spot array such that as the object is moved a distance substantially equal to a length of the spot array in the scanning direction, the spots trace a substantially continuous path on the object surface in a mechanical cross-scan direction while the irradiating and collecting steps are being performed, such that a predetermined portion of the surface of the object can be irradiated and imaged;

wherein the spot array comprises a plurality of rows and columns of spots, and the irradiating step comprises irradiating a predetermined number of rows of spots such that the spots of two adjacent ones of the columns overlap as they trace the continuous path on the object surface.

75. A method comprising the steps of:

simultaneously focusing light from a light source into an array of spots spaced apart from each other on a surface of an object to be imaged;

reflecting a first portion of the light from the light source from the array of spots at a first angle to a first detector array for collecting signals resulting from the interaction of the spots with the surface of the object to form a first image of the irradiated portions of the object surface; and reflecting a second portion of the light from the light source at a second angle different from the first angle to a second detector array for collecting signals resulting from the interaction of the spots with the surface of the object to form a second image of the irradiated portions of the object surface; and moving the object on a movable stage while the irradiating and collecting steps are being performed, such that a predetermined portion of the surface of the object can be irradiated and imaged.

76. An imager comprising:

a radiation source for simultaneously irradiating an array of spots spaced apart from each other on a surface of an object to be imaged;

a detector array for collecting signals resulting from an interaction of the spots with the surface of the object to form an image of the irradiated portions of the object surface;

a movable stage for supporting the object and moving the object such that a predetermined portion of the surface of the object can be irradiated and imaged;

a first member having an array of pin-holes corresponding to the centers of the spots of the array, the first member being disposed between the object and the detector array such that the pinholes are concentric with the spots; and a second member having an array of masks corresponding to the centers of the spots of the array, the second member being disposed between the radiation source and the surface of the object such that the masks are concentric with the spots of the spot array.

77. An imager comprising:

a radiation source for simultaneously irradiating an array of spots spaced apart from each other on a surface of an object to be imaged;

a detector array for collecting signals resulting from an interaction of the spots with the surface of the object to form an image of the irradiated portions of the object surface;

a movable stage for supporting the object and moving the object such that a predetermined portion of the surface of the object can be irradiated and imaged; and a first member having an array of masks corresponding to the centers of the spots of the array, the first member being disposed between the object and the detector array such that the masks are concentric with the spots.

78. The imager of claim 77, further comprising a second member having an array of pin-holes corresponding to the centers of the spots of the array, the second member being disposed between the radiation source and the surface of the object such that the pinholes are concentric with the spots of the spot array.

79. An imager comprising:

a light source for simultaneously irradiating an array of spots spaced apart from each other on a surface of an object to be imaged;

an array of lenses for focusing light from the light source into the array of spots;

a first detector array for collecting signals resulting from an interaction of the spots with the surface of the object to form an image of the irradiated portions of the object surface, wherein a first portion of the light from the light source is reflected from the array of spots at a first angle to the first detector array, and a second portion of the light from the light source is reflected at a second angle different from the first angle;

a second detector array for collecting signals corresponding to the second portion of the light; and a movable stage for supporting the object and moving the object such that a predetermined portion of the surface of the object can be irradiated and imaged.

80. The imager of claim 10, wherein the movable stage is for moving the object from a first position to a second position in the scanning direction such that the spots on the object surface at the second position are offset from an axis of the scanning direction and from the mechanical cross-scan direction relative to the first position.

* * * * *